United States Patent
Norimine et al.

(10) Patent No.: US 9,550,776 B2
(45) Date of Patent: Jan. 24, 2017

(54) PYRIDINYLPYRAZOLOQUINOLINE COMPOUNDS

(71) Applicant: Eisai R&D Management Co., Ltd., Bunkyo-ku, Tokyo (JP)

(72) Inventors: Yoshihiko Norimine, Tsukuba (JP); Nobuaki Sato, Tsukuba (JP); Yuki Ishihara, Tsukuba (JP); Kunitoshi Takeda, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 14/778,202

(22) PCT Filed: Apr. 3, 2014

(86) PCT No.: PCT/JP2014/059852
§ 371 (c)(1),
(2) Date: Sep. 18, 2015

(87) PCT Pub. No.: WO2014/163146
PCT Pub. Date: Oct. 9, 2014

(65) Prior Publication Data
US 2016/0289225 A1    Oct. 6, 2016

Related U.S. Application Data

(60) Provisional application No. 61/809,095, filed on Apr. 5, 2013, provisional application No. 61/809,118, filed on Apr. 5, 2013.

(51) Int. Cl.
A61K 31/44     (2006.01)
C07D 471/00    (2006.01)
(Continued)

(52) U.S. Cl.
CPC .......... *C07D 471/04* (2013.01); *A61K 31/4745* (2013.01)

(58) Field of Classification Search
CPC .......................... C07D 471/04; A61K 31/4745
(Continued)

(56) References Cited

U.S. PATENT DOCUMENTS

| 8,563,565 B2 | 10/2013 | Norimine et al. |
| 2006/0035920 A1 | 2/2006 | Boyle et al. |

(Continued)

FOREIGN PATENT DOCUMENTS

| CN | 101553491 | 10/2009 |
| CN | 101983199 | 3/2011 |

(Continued)

OTHER PUBLICATIONS

Bonkale et al., "Reduced Nitric Oxide Responsive Soluble Guanylyl Cyclase Activity in the Superior Temporal Cortex of Patients with Alzheimer's Disease," Neurosci Lett, 1995, 187:5-8.
Brandon and Rotella, "Potential CNS 8 Applications for Phosphodiesterase Enzyme Inhibitors," Annual Reports in Medicinal Chemistry, Dec. 2007, 42:3-12.
Chinese Observations in Chinese Application No. 201480016592.4, dated Nov. 4, 2015, 2 pages, with English translation.
Chinese Office Action in Chinese Application No. 201280046653.2, dated Feb. 28, 2015, 10 pages, with English translation.
(Continued)

*Primary Examiner* — Shengjun Wang
(74) *Attorney, Agent, or Firm* — Fish & Richardson P.C.

(57) ABSTRACT

A compound represented by formula (I), or a pharmaceutically acceptable salt thereof:

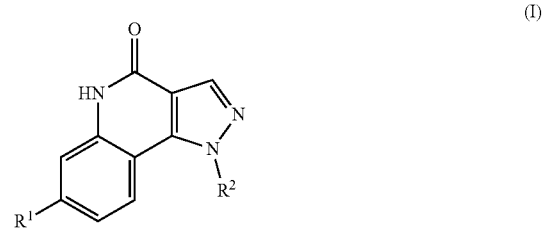

(I)

wherein $R^1$ represents a group represented by the formula:

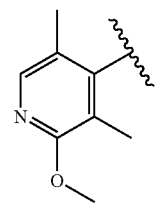

a group represented by the formula:

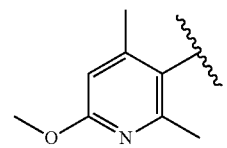

or a group represented by the formula:

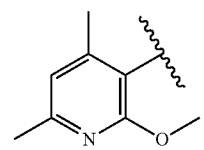

and $R^2$ represents a 3-methyltetrahydro-2H-pyran-4-yl group or 4-methoxycyclohexyl group.

11 Claims, No Drawings

(51) Int. Cl.
 C07D 471/04 (2006.01)
 A61K 31/4745 (2006.01)
(58) Field of Classification Search
 USPC .......................................... 514/293; 546/83
 See application file for complete search history.

(56) References Cited

U.S. PATENT DOCUMENTS

| | | |
|---|---|---|
| 2009/0131467 A1 | 5/2009 | Kanazawa et al. |
| 2010/0048556 A1 | 2/2010 | Okada et al. |
| 2011/0082137 A1 | 4/2011 | Giovannini et al. |
| 2011/0184000 A1 | 7/2011 | Giovannini et al. |
| 2011/0319385 A1 | 12/2011 | Kaizawa et al. |
| 2013/0085134 A1 | 4/2013 | Kaizawa et al. |
| 2013/0143907 A1 | 6/2013 | Norimine et al. |
| 2013/0225553 A1 | 8/2013 | Kaizawa et al. |
| 2013/0225572 A1 | 8/2013 | Okada et al. |

FOREIGN PATENT DOCUMENTS

| | | |
|---|---|---|
| EP | 2103613 | 9/2009 |
| JP | H5-132484 | 5/1993 |
| JP | H9-506634 | 6/1997 |
| JP | 2006-045118 | 2/2006 |
| JP | 2011-516454 | 5/2011 |
| JP | 2013-067595 | 4/2013 |
| JP | 5546693 | 5/2014 |
| WO | WO 95/32205 | 11/1995 |
| WO | WO 2007/032466 | 3/2007 |
| WO | WO 2008/072779 | 6/2008 |
| WO | WO 2008/139293 | 11/2008 |
| WO | WO 2009/121919 | 10/2009 |
| WO | WO 2010/101230 | 9/2010 |
| WO | WO 2012/033144 | 3/2012 |
| WO | WO 2013/045400 | 4/2013 |
| WO | WO 2013/051639 | 4/2013 |

OTHER PUBLICATIONS

Chinese Office Action in Chinese Application No. 201480016592.4, dated Oct. 16, 2015, 2 pages, with English translation.
Columbian Office Action in Columbian Application No. 14-059034, dated Mar. 10, 2015, 13 pages, with English translation.
Domek-Lopacinska and Strosznajder, "Cyclic GMP Metabolism and its Role in Brain Physiology," J Phys and Pharma, 2005, 56(S2):15-34.
Extended European Search Report in European Application No. 12837953.4, dated Jan. 27, 2015, 10 pages.
Fisher et al., "Isolation and Characterization of PDE9A, a Novel Human cGMP-specific Phosphodiesterase," J Biol Chem, 1998, 273(25):15559-15564.
International Preliminary Report on Patentability in International Application No. PCT/JP2012/075748, dated Apr. 17, 2014, 10 pages.
International Preliminary Report on Patentability in International Application No. PCT/JP2014/059852, dated Oct. 15, 2015, 8 pages.
International Preliminary Report on Patentability in International Application No. PCT/JP2014/059853, dated Oct. 15, 2015, 7 pages.
International Search Report in International Application No. PCT/JP2012/075748, dated Nov. 20, 2012, 2 pages.
Israeli Office Action in Israeli Application No. 231650, dated Jul. 16, 2014, 4 pages, with English translation.
Japanese Notice of Allowance in Japanese Application No. P2013-537544, dated Apr. 30, 2014, 6 pages, with English translation.
Japanese Office Action in Japanese Application No. P2014-538559, dated Sep. 30, 2014, 4 pages, with English translation.
New Zealand Office Action in New Zealand Application No. 622594, dated Feb. 4, 2015, 2 pages.
Pakistani Office Action in Pakistani Application No. 672/2012, dated Feb. 14, 2013, 8 pages.
Response to Chinese Office Action dated Feb. 28, 2015 in Chinese Application No. 201280046653.2, dated Apr. 28, 2015, 16 pages, with English translation.
Response to Columbian Office Action dated Mar. 10, 2015 in Columbian Application No. 14-059034, dated Jul. 16, 2015, 23 pages, with English translation.
Response to Extended European Search Report dated Jan. 27, 2015 in European Application No. 12837953.4, dated May 15, 2015, 22 pages.
Response to Israeli Office Action Dated Jul. 16, 2014 in Israeli Application No. 231650, dated Nov. 6, 2014, 8 pages, with English translation.
Response to New Zealand Office Action dated Feb. 4, 2015 in New Zealand Application No. 622594, dated May 22, 2015, 16 pages.
Response to Vietnamese Office Action dated Nov. 25, 2015 in Vietnamese Application No. 1-2015-03459, dated Dec. 17, 2015, 21 pages, with English translation.
South American Notice of Allowance in South American Application No. 2014/02439, dated Jan. 21, 2015, 3 pages.
Takano et al., "Oral Absorption of Poorly Water-Soluble Drugs: Computer Simulation of Fraction Absorbed in Humans From a Miniscale Dissolution Test," Pharm Res, Jun. 2006, 23(6):1144-1156.
United States Notice of Allowance in U.S. Appl. No. 13/644,745, dated Jun. 10, 2013, 13 pages.
United States Office Action in U.S. Appl. No. 13/644,745, dated Mar. 26, 2013, 8 pages.
Van der Staay et al., "The Novel Selective PDE9 Inhibitor BAY 73/6691 Improves Learning and Memory in Rodents," Neurophannacology, 2008, 55(5):908-918.
Vietnamese Office Action in Vietnamese Application No. 1-2015-03459, dated Nov. 25, 2015, 2 pages, with English translation.
Wang and Robinson, "Cyclic GMP-Dependent Protein Kinase and Cellular Signaling in the Nervous System," J Neurochem, 1997, 68(2):443-459.
Response to Office Action in Chilean Application No. 2014-00821, dated Dec. 16, 2015, 6 pages, with English translation.
Office Action in Israeli Application No. 241796, dated Jan. 24, 2016, 5 pages, with English translation.
Request to Amend Application Before Grant in Singapore Application No. 11201400717Q, dated Feb. 12, 2016, 9 pages.
Australian Notice of Allowance in Application No. 2012319549, dated Jul. 19, 2016, 3 pages.
Australian Office Action in Application No. 2012319549, dated Jun. 1, 2016, 7 pages.
Australian Response to Examination Report in Application No. 2012319549, dated Jul. 8, 2016, 6 pages.
Chinese Office Action in Application No. 201480016592.4, dated May 12, 2016, 12 pages, with English translation.
Chinese Office Action in Application No. 201480017423.2, dated Mar. 1, 2016, 10 pages, with English translation.
Chinese Submission Documents in Application No. 2014/0017423.2, dated Jul. 4, 2016, 6 pages, with English translation.
European Response to Office Action in Application No. 14780073.4, dated May 11, 2016, 5 pages.
European Response to Office Action in Application No. 14780139.3, dated May 10, 2016, 4 pages.
European Search Report in Application No. 14780073.4, dated Jul. 28, 2016, 4 pages.
European Search Report in Application No. 14780139.3, Jul. 13, 2016, 5 pages.
Filipino Office Action in Application No. 1-2014-500580, dated Jun. 17, 2016, 3 pages.
Filipino Submission Documents in Application No. 1-2014-500580, dated Jul. 21, 2016, 5 pages.
GCC Office Action in Application No. GC2012-22447, dated Apr. 21, 2016, 4 pages.
Israeli Notice of Allowance in Application No. 231650, dated Feb. 10, 2016, 5 pages, with English translation.
Israeli Response to Office Action in Application No. 241695, dated May 23, 2016, 4 pages.
Israeli Response to Office Action in Application No. 241796, dated May 23, 2016, 4 pages, with English translation.

(56) References Cited

OTHER PUBLICATIONS

Russian Response to Office Action in Application No. 2014112931, dated Jul. 26, 2016, 23 pages, with English translation.
Singapore Notice of Allowance in Application No. 11201400717Q, dated May 26, 2016, 4 pages.
Taiwanese Office Action in Application No. 101136747, dated Apr. 22, 2016, 5 pages, with English translation.
Thai Submission Documents in Application No. 1401001864, dated Feb. 15, 2016, 352 pages, with English translation.
Response to Office Action in Chilean Application No. 2014-00821, dated Aug. 19, 2015, 26 pages, with English translation.
Office Action in Chilean Application No. 2014-00821, dated Oct. 29, 2015, 11 pages, with English translation.
Office Action in Israeli Application No. 241695, dated Jan. 24, 2016, 5 pages, with English translation.

SEQUENCE LISTING

<160> NUMBER OF SEQ ID NOS: 2

<210> SEQ ID NO 1
<211> LENGTH: 22
<212> TYPE: DNA
<213> ORGANISM: Artificial
<220> FEATURE:
<223> OTHER INFORMATION: hPDE9-1

<400> SEQUENCE: 1
aggatgggat ccggctcctc ca                                            22

<210> SEQ ID NO 2
<211> LENGTH: 21
<212> TYPE: DNA
<213> ORGANISM: Artificial
<220> FEATURE:
<223> OTHER INFORMATION: hPDE9A-3

<400> SEQUENCE: 2
caggcacagt ctccttcact g                                             21

PYRIDINYLPYRAZOLOQUINOLINE COMPOUNDS

TECHNICAL FIELD

The present invention relates to pyridinylpyrazoloquinoline compounds having inhibitory activity against phosphodiesterase 9 (PDE9), and pharmaceutically acceptable salts thereof, and pharmaceutical applications thereof.

BACKGROUND ART

Cyclic guanosine monophosphate (hereinafter, referred to as cGMP) functioning as a second messenger in cells is known to play an important role in various physiological functions including learning and memory behaviors.

On the postsynaptic site of the brain neural circuits, nitrogen monoxide (hereinafter, referred to as NO) biosynthesized by a nitrogen monoxide synthetase activates a guanylate cyclase, which is a cGMP synthetase. The activated guanylate cyclase biosynthesizes cGMP from guanosine triphosphate. The cGMP activates a cGMP-dependent protein kinase (hereinafter, referred to as PKG) to phosphorylate various proteins participating in synapse plasticity. The activation of the NO/cGMP/PKG cascade is known to participate in the induction of synapse plasticity (Long Term Potentiation; hereinafter, referred to as LTP) of the hippocampus known as a neural substrate for learning and memory behaviors (for example, see Non Patent Literature 1). A medicine activating the signal transmission of the cascade is known to improve LTP of the hippocampus and the learning behavior of animals, while a medicine inhibiting the cascade is known to exhibit the opposite action (Non Patent Literature 2). Therefore, from these findings, an increase in cGMP in the brain is anticipated to lead to an improvement of learning and memory behaviors.

cGMP is metabolized to 5'-GMP having no PKG activation action by a phosphodiesterase (hereinafter, referred to as PDE). The PDE is known to have 11 families, and PDE9 is known to metabolize specifically cGMP, and to be expressed in the brain, the spleen, the small intestine and the like (for example, see Non Patent Literature 3). That is, inhibition of PDE9 is anticipated to increase cGMP in brains. It is reported that a PDE9 inhibitor actually enhances hippocampus LTP, and improves the learning and memory behaviors in a novel-object recognition test/passive avoidance learning test or the like in animals (Non Patent Literature 4). Clinically, guanylate cyclase activity decreases and possibility of a decrease in the cGMP level is indicated in the superior temporal cortex of Alzheimer's disease patients, (Non Patent Literature 5). Therefore, the PDE9 has a possibility of having many close relations with pathologies of neurodegenerative diseases and psychiatric diseases, particularly with pathologies of cognitive dysfunctions and the like in the Alzheimer's disease, such as Alexander's disease, Alpers' disease, Alzheimer's disease, amyotrophic lateral sclerosis (ALS; known as Lou Gehrig's disease or motor neuron disease), ataxia-telangiectasia, Batten's disease (known also as Spielmeyer-Vogt-Sjogren-Batten's disease), Binswanger's dementia (subcortical angiosclerotic encephalopathy), bipolar disorder, bovine spongiform encephalopathy (BSE), Canavan's disease, chemotherapy induction dementia, Cockayne's syndrome, corticobasal degeneration, Creutzfeldt-Jakob's disease, depression, Down's syndrome, frontotemporal lobe degeneration (including frontotemporal dementia, semantic dementia and progressive nonfluent aphasia), Gerstmann-Straussler-Scheinker's disease, glaucoma, Huntington's disease (chorea), HIV related dementia, hyperkinesis, Kennedy's disease, Korsakoff's syndrome (amnesic confabulation syndrome), Krabbe's disease, Lewy-bodies dementia, progressive logopenic aphasia, Machado-Joseph's disease (spinocerebellar ataxia type 3), multiple sclerosis, multiple atrophy (olivopontocerebellar atrophy), myasthenia gravis, Parkinson's disease, Pelizaeus-Merzbacher's disease, Pick's disease, dementia presenilis (slight cognitive impairment), primary lateral sclerosis, primary progressive aphasia, radiation-induced dementia, Refsum's disease (phytanic acid storage disease), Sandhoff's disease, Schilder's disease, schizophrenia, semantic dementia, senile dementia, Shy-Drager syndrome, spinocerebellar ataxia, spinal muscle atrophy, Steele-Richardson-Olszewski's disease (progressive supranuclear palsy), and vascular amyloidosis and vascular dementia (multiple infarct dementia).

Recently, the following compound has been known which has PDE9 inhibitory activity and has a purpose of prevention or therapy of Alzheimer's disease (Patent Literature 1).

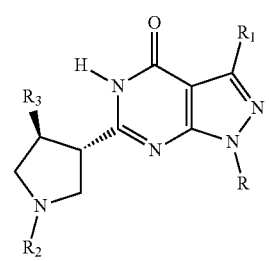

(1)

The above compound is a pyrazolopyrimidine derivative, and a compound having a structure totally different from a pyrazoloquinoline skeleton.

On the other hand, as a compound having a pyrazoloquinoline skeleton, the following compound described in Patent Literature 2 is known.

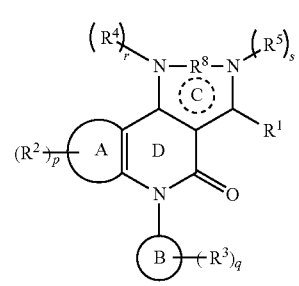

(1)

wherein a ring A is a benzene ring or the like; and $R^6$ is a direct bond or the like.

However, a ring B in the above compound denotes a benzene ring or the like. Although it is stated that the above compound has inhibitory activity against PDE4 and is used for various types of inflammatory diseases, there is no description for implication of the inhibitory activity against PDE9, and the like.

As compounds having PDE9 inhibitory activity, the following compounds described in Patent Literature 3 and Patent Literature 4 are known.

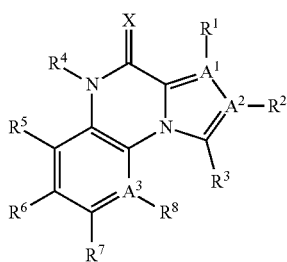

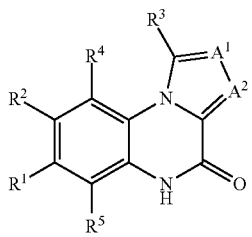

Any of the above compounds is a quinoxaline derivative, and is a compound having a structure totally different from a pyrazoloquinoline skeleton.

As a compound having a pyrazoloquinoline skeleton and having PDE9 inhibitory activity, the following compound described in Patent Literature 5 is known.

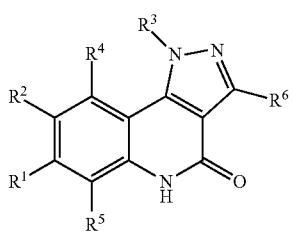

wherein either $R^1$ or $R^2$ is a group represent by the formula

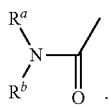

The structure of the above compound is restricted in $R^1$ and $R^2$, thus the compound is a compound having a structure totally different from the compound of the present invention.

CITATION LIST

Patent Literatures

[Patent Literature 1] WO 2008/139293
[Patent Literature 2] WO 2007/032466
[Patent Literature 3] WO 2008/072779
[Patent Literature 4] WO 2010/101230
[Patent Literature 5] WO 2012/033144

Non-Patent Literature

[Non Patent Literature 1] Domek-Lopacinska et al., "Cyclic GMP metabolism and its role in brain physiology", J Physiol Pharmacol., vol. 56, Suppl 2: pp. 15-34, 2005

[Non Patent Literature 2] Wang X., "Cyclic GMP-dependent protein kinase and cellular signaling in the nervous system", J. Neurochem., vol. 68, pp. 443-456, 1997

[Non Patent Literature 3] Fisher et al., "Isolation and characterization of PDE9A, a novel human cGMP-specific phosphodiesterase", J. Biol. Chem., vol. 273: pp. 15559-15564, 1998

[Non Patent Literature 4] van der Staay et al., "The novel selective PDE9 inhibitor BAY 73-6691 improves learning and memory in rodents", Neuropharmacology, vol. 55: pp. 908-918, 2008

[Non Patent Literature 5] Bonkale et al., "Reduced nitric oxide responsive soluble guanylyl cyclase activity in the superior temporal cortex of patients with Alzheimer's disease", Neurosci. Lett., vol 187, pp. 5-8, 1995

SUMMARY OF INVENTION

Technical Problem

It is an object of the present invention to provide a novel compound or pharmaceutically acceptable salt thereof having PDE9 inhibitory action, and a pharmaceutical composition containing the same.

Solution to Problem

As a result of exhaustive studies to solve the above-mentioned problems, the present inventors have found a novel pyridinylpyrazoloquinoline compound or pharmaceutically acceptable salt thereof having PDE9 inhibitory action.

That is, the present invention relates to the following <1> to <14>.

<1> A compound represented by formula (I), or a pharmaceutically acceptable salt thereof:

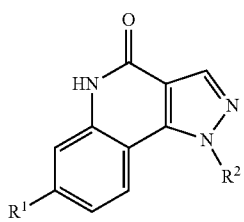

wherein $R^1$ is a group represented by the formula:

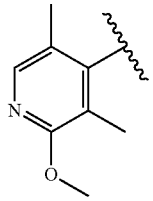 [SMILES: *c1c(C)cnc(OC)c1C]

a group represented by the formula:

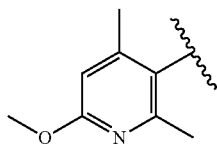

or a group represented by the formula:

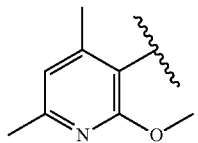

and R² is a 3-methyltetrahydro-2H-pyran-4-yl group or 4-methoxycyclohexyl group.

<2> A compound or a pharmaceutically acceptable salt thereof according to <1>, wherein the compound is represented by formula (II):

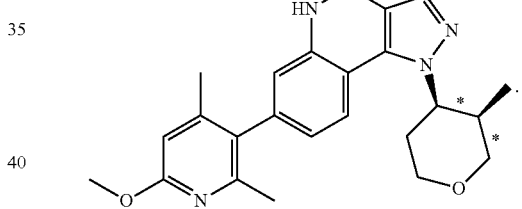

(II)

wherein R³ is a group represented by the formula:

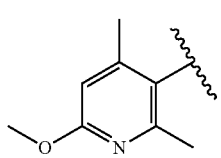

or a group represented by the formula:

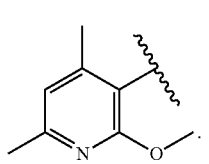

<3> A compound or a pharmaceutically acceptable salt thereof according to <1>, wherein the compound is represented by formula (III):

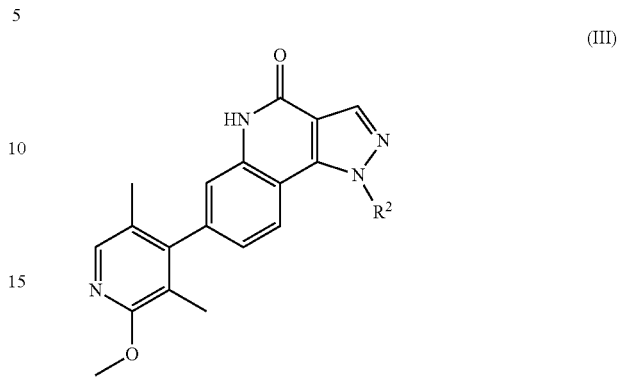

(III)

wherein R² is a 3-methyltetrahydro-2H-pyran-4-yl group or 4-methoxycyclohexyl group.

<4>(−)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((−)-cis) or a pharmaceutically acceptable salt thereof:

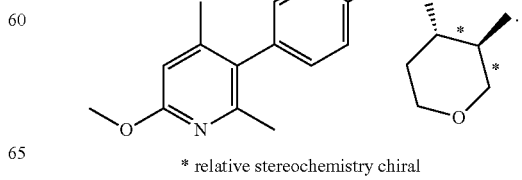

* relative stereochemistry chiral

<5>(−)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4 (5H)-one ((−)-trans) or a pharmaceutically acceptable salt thereof:

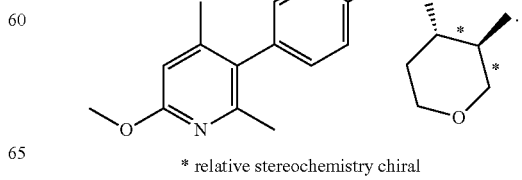

* relative stereochemistry chiral

<6> (+7-(2-Methoxy-4,6-dimethylpyridin-3-yl)-1-((3R*, 4S*)-3-methyltetrahydro-2H-pyran-4-yl)-1H-pyrazolo[4, 3-c]quinoline-4(5H)-one ((−)-trans) or a pharmaceutically acceptable salt thereof:

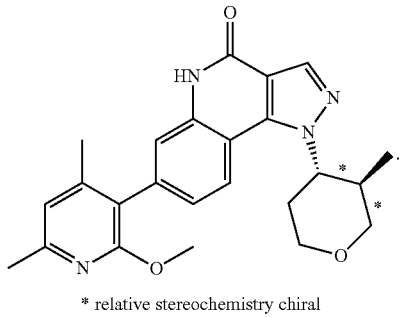

* relative stereochemistry chiral

<7> (−)-7-(2-Methoxy-3,5-dimethylpyridin-4-yl)-1-((3R*, 4R*)-3-methyltetrahydro-2H-pyran-4-yl)-1H-pyrazolo[4, 3-c]quinoline-4(5H)-one ((−)-cis) or a pharmaceutically acceptable salt thereof:

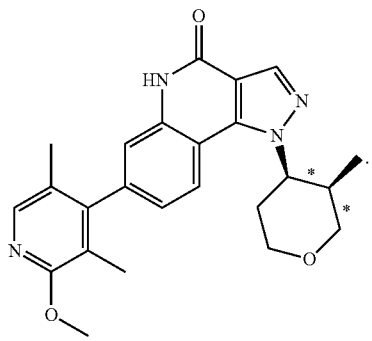

* relative stereochemistry chiral

<8> 7-(2-Methoxy-3,5-dimethylpyridin-4-yl)-1-(trans-4-methoxycyclohexyl)-1H-pyrazolo[4,3-c]quinoline-4(5H)-one or a pharmaceutically acceptable salt thereof:

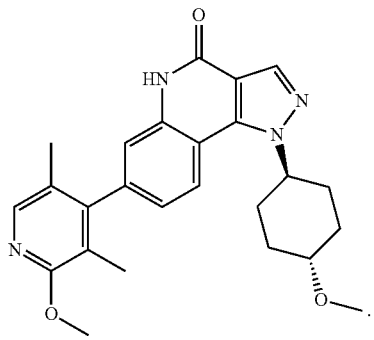 [SMILES: COc1ncc(C)c(-c2ccc3c(c2)[nH]c(=O)c2cnn([C@H]4CC[C@H](OC)CC4)c23)c1C]

<9> A pharmaceutical composition comprising a compound or a pharmaceutically acceptable salt according to <1> as an active ingredient.

<10> A pharmaceutical composition according to <9>, which is a PDE9 inhibitor.

<11> A pharmaceutical composition according to <9> for increasing intracerebral cGMP concentration.

<12> A cognitive impairment improving agent in Alzheimer's disease, comprising a compound or a pharmaceutically acceptable salt thereof according to <1>.

<13> A method for improving cognitive impairment in Alzheimer's disease, comprising administering a compound or a pharmaceutically acceptable salt thereof according to <1> to a patient.

<14> A compound or a pharmaceutically acceptable salt thereof according to <1> for use for improving cognitive impairment in Alzheimer's disease.

Advantageous Effects of Invention

The pyridinylpyrazoloquinoline compounds (hereinafter, referred to as a compound (I)) represented by the formula (I) or pharmaceutically acceptable salt thereof according to the present invention has PDE9 inhibitory action as shown in activity data in Pharmacological Test Example described later. The compound (I) according to the present invention mostly exhibits an $IC_{50}$ value of 1,000 nM or below as the PDE9 inhibitory action, and a compound exhibiting an $IC_{50}$ value of 100 nM or below is preferable.

The compound (I) according to the present invention has PDE9 inhibitory action, so that the intracerebral cGMP concentration is anticipated to be elevated. The PDE9 inhibitory action and the increase in cGMP lead to the improvement of learning and memory behaviors, and the compound (I) has a potential use of a therapeutic agent for cognitive dysfunctions and the like in Alzheimer's disease.

DESCRIPTION OF EMBODIMENTS

Hereinafter, the content of the present invention will be described in detail.

Throughout the present specification, the structural formulas for the compounds will show only one specific isomer for convenience, but the invention includes all isomers such as geometric isomers, optical isomers, stereoisomers and tautomers implied by the compound structures, as well as their isomer mixtures, and the compounds may therefore be any of the isomers or mixtures thereof in any desired proportion, without being limited to the formulas that are shown for convenience. Thus, for example, the compounds of the invention may exist as optically active forms or racemic mixtures, all of which are included without limitations according to the invention, and whether racemic mixtures or optically active forms, they may be used as mixtures with the optically active forms in any desired proportion. It will be understood, however, that some isomers or racemic mixtures or other mixtures of isomers may exhibit more activity than others.

Polymorphic crystals may also exist, and there may be used any crystal form or a mixture thereof without any restrictions, as well as amorphous forms, and the compounds of the invention also include both anhydrate and solvate (especially hydrate).

Compounds of the formula (I) labeled with isotopes are also included in the present invention. A compound labeled with an isotope is the same as the compound (I), except that one or more atoms are replaced by atoms having atomic masses or mass numbers different from those usually found in the natural world. Isotopes which can be incorporated in the compound according to the present invention are isotopes of, for example, hydrogen, carbon, nitrogen, oxygen, fluorine, phosphorus, sulfur, iodine, and chlorine, and include $^{2}H$, $^{3}H$, $^{11}C$, $^{14}C$, $^{15}N$, $^{18}O$, $^{18}F$, $^{32}P$, $^{35}S$, $^{123}I$ and $^{125}I$.

The above isotope-labeled compounds, for example, compounds in which radioisotopes such as $^3$H, and/or $^{14}$C are incorporated, are useful for the tissue distribution assay of medicines and/or substrates. $^3$H and $^{14}$C are considered to be useful for ease of the preparation and detection thereof. Isotopes $^{11}$C and $^{18}$F are considered to be useful for PET (positron-emission tomography); and an isotopes $^{125}$I is considered to be useful for SPECT (single photon emission computed tomography); and all are useful for brain imaging. The replacement by a heavier isotope such as $^2$H causes some type of therapeutic advantages including an increase in the in-vivo half-life period or a decrease in the necessary dose due to higher metabolic stability, and therefore, is considered to be useful under some situation. The above isotope-labeled compounds can be similarly prepared by carrying out procedures disclosed in the following Examples by using reagents labeled with isotopes easily utilizable in place of reagents not labeled with an isotope.

Hereinafter, the meanings of terms, symbols and the like described in the present specification will be described, and the present invention will be described in detail.

The definitions and preferable examples of R$^1$ and R$^2$ in the compound represented by the formula (I) will be explained below.

R1 is a group represented by the formula:

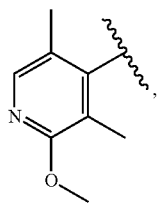

a group represented by the formula:

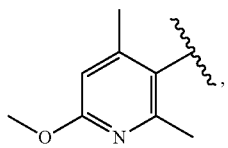 [SMILES: *c1c(C)cc(OC)nc1C]

or a group represented by the formula:

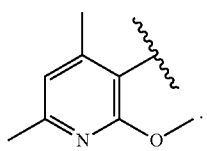

R$^2$ is a 3-methyltetrahydro-2H-pyran-4-yl group or 4-methoxycyclohexyl group.

A "pharmaceutically acceptable salt" in the present specification is not especially limited as long as a salt formed with the compound according to the present invention, and specific examples include inorganic acid salts, organic acid salts, inorganic base salts, organic base salts, and acidic or basic amino acid salts.

If only a "pharmaceutically acceptable salt" in the present specification is a salt formed in a suitable ratio unless there is any especially limiting description, the number of acid molecules per one molecule of the compound in a formed salt, although being not especially limited, is preferably about 0.1 to about 5 molecules, more preferably about 0.5 to about 2 molecules, and still more preferably about 0.5, about 1 or about 2 molecules, per one molecule of the compound.

Preferable examples of inorganic acid salts include hydrochlorides, hydrobromides, sulfates, nitrates and phosphates, and preferable examples of organic acid salts include acetates, succinates, fumarates, maleates, tartrates, citrates, lactates, stearates, benzoates, methanesulfonates, p-toluenesulfonates and benzenesulfonates.

Preferable examples of inorganic base salts include alkaline metal salts such as sodium salts and potassium salts, alkaline earth metal salts such as calcium salts and magnesium salts, aluminum salts, and ammonium salts, and preferable examples of organic base salts include diethylamine salts, diethanolamine salts, meglumine salts and N,N'-dibenzylethylenediamine salts.

Preferable examples of acidic amino acid salts include aspartates and glutamates, and preferable examples of basic amino acid salts include arginine salts, lysine salts and ornithine salts.

[Pharmaceutical preparation] A compound of the formula (I) according to the present invention or a pharmaceutically acceptable salt thereof can be pharmaceutically prepared by a conventional method, and the dosage form can be made, for example, an oral preparation (tablet, granule, powder, capsule, syrup, or the like), an injection (for intravenous administration, for intramuscular administration, for subcutaneous administration, for intraperitoneal administration, and for others), and an external preparation (endermic preparation (ointment, patch, and the like), eyedrops, nasal drops, suppository, and the like).

In the case of producing an oral solid preparation, to a compound of the formula (I) or a pharmaceutically acceptable salt thereof, as required, an excipient, a binder, a disintegrant, a lubricant, a colorant and the like are added, and a tablet, a granule, a powder and a capsule can be produced by conventional methods. The tablet, granule, powder, capsule and the like, as required, may be film-coated.

Examples of the excipient include lactose, cornstarch and crystalline cellulose; examples of the binder include hydroxypropyl cellulose and hydroxypropyl methyl cellulose; examples of the disintegrant include carboxymethyl cellulose calcium and croscarmellose sodium; examples of the lubricant include magnesium stearate and calcium stearate; examples of the colorant include titanium oxide; and examples of the film coating agent include hydroxypropyl cellulose, hydroxypropyl methyl cellulose and methyl cellulose, but these additives are of course not limited to these examples.

These solid preparations such as tablets, capsules, granules and powders can each contain usually 0.001 to 99.5% by weight, preferably 0.01 to 90% by weight or the like, of a compound of the formula (I) or a pharmaceutically acceptable salt thereof.

In the case of producing an injection (for intravenous administration, for intramuscular administration, for subcutaneous administration, for intraperitoneal administration, and for others), to a compound of the formula (I) or a pharmaceutically acceptable salt thereof, as required, a pH regulator, a buffer agent, a suspending agent, a solubilizer, an antioxidant, a preservative (antiseptic), an isotonic agent, and the like are added, and an injection can be produced by a conventional method. The preparations may be lyophilized to be made extemporaneous dissolution-type lyophilized preparations.

Examples of the pH regulator and the buffer agent include organic acids or inorganic acids or salts thereof; examples of the suspending agent include methyl cellulose, Polysorbate 80 and carboxymethyl cellulose sodium; examples of the solubilizer include Polysorbate 80 and polyoxyethylene sorbitan monolaurate; examples of the antioxidant include α-tocopherol; examples of the preservative include methyl paraoxybenzoate and ethyl paraoxybenzoate; and examples of the isotonic agent include glucose, sodium chloride and mannitol, but these additives are of course not limited to these examples.

These injections can each contain usually 0.000001 to 99.5% by weight, preferably 0.00001 to 90% by weight or the like, of a compound of the formula (I) or a pharmaceutically acceptable salt thereof.

In the case of producing an external preparation, a basis raw material is added to a compound of the formula (I) or a pharmaceutically acceptable salt thereof, and as required, for example, the preservative, a stabilizer, the pH regulator, the antioxidant, the colorant and the like are added, and for example, an endermic preparation (ointment, patch, and the like), eyedrops, nasal drops, suppository, and the like can be produced by conventional methods.

As basis raw materials to be used, various raw materials usually used, for example, for medicines, quasi-drugs and cosmetics can be used. Specific examples thereof include raw materials such as animal and vegetable oils, mineral oils, ester oils, waxes, emulsifiers, higher alcohols, fatty acids, silicon oils, surfactants, phospholipids, alcohols, polyhydric alcohols, water-soluble polymers, clay minerals and purified water.

These external preparations can each contain usually 0.000001 to 99.5% by weight, preferably 0.00001 to 90% by weight or the like, of a compound of the formula (I) or a pharmaceutically acceptable salt thereof.

The compound according to the present invention can be made a chemical probe to trap a target protein of a physiologically active low-molecular compound. That is, the compound according to the present invention can be converted to an affinity chromatography probe, a photoaffinity probe and the like by introducing a labeling group, a linker or the like to a moiety different from a structural moiety essential to develop the activity of the compound, by the technique described in J. Mass Spectrum. Soc. Jpn., Vol. 51, No. 5, 2003, p. 492-498, WO2007/139149, or the like.

Examples of the labeling group, the linker or the like used in a chemical probe include groups shown in the group consisting of the following (1) to (5):
(1) protein labeling groups such as photoaffinity labeling groups (for example, a benzoyl group, a benzophenone group, an azido group, a carbonyl azido group, a diaziridine group, an enone group, a diazo group and a nitro group), and chemoaffinity groups (for example, ketone groups whose alpha-carbon atom is replaced by a halogen atom, a carbamoyl group, an ester group, an alkylthio group, a Michael acceptor of an α,β-unsaturated ketone, an ester or the like, and an oxirane group);
(2) cleavable linkers such as —S—S—, —O—Si—O—, monosaccharides (a glucose group, a galactose group, and the like), and disaccharides (lactose and the like), and oligopeptide linkers cleavable by an enzymatic reaction;
(3) fishing tag groups such as biotin and a 3-(4,4-difluoro-5,7-dimethyl-4H-3a,4a-diaza-4-bora-s-indacen-3-yl)propionyl group;
(4) radioactive labeling groups of $^{125}I$, $^{32}P$, $^{3}H$, $^{14}C$ or the like; fluorescent labeling groups such as fluorescein, rhodamine, dansyl, umbelliferone, 7-nitrofurazanyl, and 3-(4,4-difluoro-5,7-dimethyl-4H-3a,4a-diaza-4-bora-s-indecen-3-yl)propionyl group; chemiluminescent groups such as luciferin and luminol; and markers capable of detecting heavy metal ions such as lanthanide metal ions and radium ions; and
(5) groups to be attached to solid carriers such as glass beads, glass beds, microtiter plates, agarose beads, agarose beds, polystyrene beads, polystyrene beds, nylon beads and nylon beds.

Probes prepared by introducing labeling groups selected from the group consisting of the above (1) to (5), or the like, to the compound according to the present invention by methods described in the above literatures or the like can be used as chemical probes to identify labeled proteins useful for search and the like of new drug discovery targets.

EXAMPLES

The compound (I) according to the present invention can be produced, for example, by methods described in the following Examples, and the effects of the compound can be verified by methods described in the following Test Examples. However, these are only exemplifications, and the present invention is not limited to the following specific examples in any case, and changes and modifications may be made without departing from the scope of the present invention.

It is indicated that compounds for which literature names or the like are described were produced according to the literatures or the like.

Abbreviations used in the present specification are common ones well-known by those skilled in the art. The following abbreviations will be used in the present specification.
CDI: 1,1'-carbonyldiimidazole
DCM: dichloromethane
DIPEA: N,N-diisopropylethylamine
DMF: N,N-dimethylformamide
DMF-DMA: N,N-dimethylformamide dimethyl acetal
DMSO: dimethylsulfoxide
DTT: dithiothreitol
EDC: 1-ethyl-3-(3-dimethylaminopropyl)carbodiimide hydrochloride
EDTA: ethylenediaminetetraacetic acid
EGTA: glycol ether diamine tetraacetic acid
HOBT: 1-hydroxybenzotriazole
KTB: potassium tert-butoxide
MTBE: t-butylmethylether
n-: normal
p-: para
Pd(dppf)Cl$_2$ DCM complex: [1,1'-bis(diphenylphosphine)ferrocene]dichloropalladium(II) DCM complex
Pd(PPh$_3$)$_4$: tetrakis(triphenylphosphine)palladium(0)
t-: tertiary
TEA: triethylamine
TFA: trifluoroacetic acid
THF: tetrahydrofuran
Tris: trishydroxymethylaminomethane
$^1$H-NMR: proton nuclear magnetic resonance spectrometry
LC-MS: liquid chromatography-mass spectrometry "Room temperature" in the following Examples and Preparation Examples usually indicates about 10° C. to about 35° C. % indicates weight percent unless otherwise specified.

The chemical shift of the proton nuclear magnetic resonance spectrum is recorded in δ units (ppm) from tetramethylsilane; and the coupling constant is recorded in hertz (Hz). The abbreviations of splitting patterns are as follows: s: singlet, d: doublet, t: triplet, q: quartet, m: multiplet, brs: broad singlet and brd: broad doublet.

For the optical resolution of a compound, Parallex Flex®, made by Biotage, (column: one of CHIRALPAK® AD-H, IA, IB and IC made by Daicel Corp., and CHIRALCEL® OD-H and OJ-H made by Daicel Corp.; column size 2 cm Φ×25 cm) was used. The optical rotation (+/−) was measured by an OR-2090 chiral detector (Hg—Xe lamp, 150 W) made by JASCO.

With respect to the chromatography, in the case where there is a description as silica gel column chromatography, was used a Parallel Prep, made by Yamazen Corp., (column: Hi-Flash® Column (Silicagel), made by Yamazen Corp., size: one of S (16×60 mm), M (20×75 mm), L (26×100 mm), 2 L (26×150 mm), and 3 L (46×130 mm)) or spherical shape silica gel for chromatography PSQ60B® made by Fuji Silysia Chemical Ltd., silica gel for chromatography BW-300® made by Fuji Silysia Chemical Ltd., Wakogel® C-200 made by Wako Pure Chemical Industries, Ltd. or Silica Gel 60® (70-230 mesh) made by Merck Ltd. Japan. In the case where there is a description as NH silica gel column chromatography, was used a Parallel Prep, made by Yamazen Corp., (column: Hi-Flash® Column (Amino), made by Yamazen Corp., size: one of S (16×60 mm), M (20×75 mm), L (26×100 mm), 2 L (26×150 mm), and 3 L (46×130 mm)) or NH silica gel (200-350 mesh) made by Fuji Silysia Chemical Ltd.

(±)- indicates a racemic mixture, and (+)- and (−)- indicate the (+) type and the (−) type of an enantiomer, respectively.

The names of following compounds were used as those indicated in "E-notebook" ver. 12 (Perkin Elmer) except commonly used reagents.

Production Example 1

Synthesis of
3-bromo-6-methoxy-2,4-dimethylpyridine

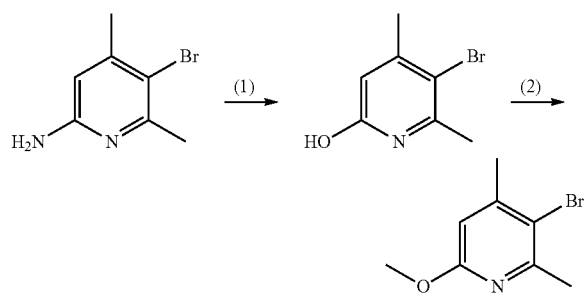

(1) Synthesis of 5-bromo-4,6-dimethylpyridin-2-ol

2-Amino-5-bromo-4,6-dimethylpyridine (15 g) was dissolved in a mixed solution of sulfuric acid (14.2 mL) and water (212 mL). A solution of sodium nitrite (6.18 g) in water (31 mL) was added to the solution at 0° C. The reaction mixture was stirred for 1 hour at room temperature and extracted with chloroform. The organic layer was dried over anhydrous magnesium sulfate and the desiccant was filtered out. The filtrate was concentrated under reduced pressure, MTBE was added to the residue, and the precipitated solid was deposited and then filtered out. The obtained solid was rinsed with MTBE to obtain the title compound (13.7 g).
ESI-MS m/z 204 [M+H]+

(2) Synthesis of
3-bromo-6-methoxy-2,4-dimethylpyridine

A mixture of 5-bromo-4,6-dimethylpyridin-2-ol (7 g), methyl iodide (21.6 mL) and silver carbonate (19.1 g) in a chloroform (140 mL) was stirred at room temperature for 36 hours. The reaction mixture was supplied to a silica gel pad, and was eluted with a mixed solvent (ethyl acetate: n-heptane =2:8). The obtained fraction was concentrated under reduced pressure to obtain the title compound (6.98 g).
$^1$H-NMR (400 MHz, CDCl$_3$) δ (ppm): 2.32-2.35 (m, 3H), 2.56-2.58 (m, 3H), 3.88 (s, 3H), 6.43-6.48 (m, 1H).
ESI-MS m/z 216 [M+H]+

Production Example 2

Synthesis of
3-bromo-2-methoxy-4,6-dimethylpyridine

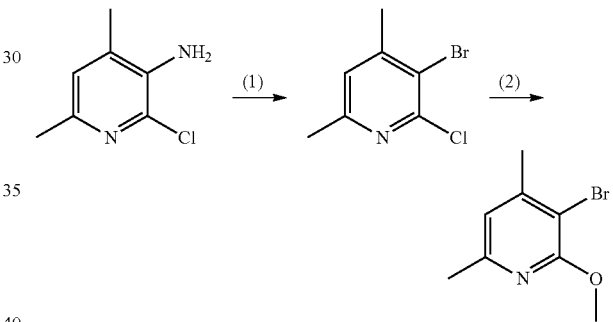

(1) Synthesis of
3-bromo-2-chloro-4,6-dimethylpyridine

2-Chloro-4,6-dimethylpyridine-3-amine (2.85 g) was dissolved in hydrobromic acid (15 mL, 48% aqueous solution), and was cooled to 0° C. A solution of sodium nitrite (1.51 g) in water (2 mL) was then slowly added dropwise to the solution, and the mixture was stirred at 0° C. for 15 minutes. A suspension of copper(I) bromide (4.18 g) in hydrobromic acid (5 mL, 48% aqueous solution) was added dropwise to this solution, and after stirring at 0° C. for 10 minutes, it was further stirred at 60° C. for 1 hour. The reaction mixture was cooled to room temperature, and then was extracted with ethyl acetate. The organic layer was directly supplied to an NH-silica gel pad and was eluted with ethyl acetate. The obtained fraction was concentrated under reduced pressure and the residue was purified by NH silica gel column chromatography (ethyl acetate/n-heptane, 0% to 30%) to obtain the title compound (2.97 g).
ESI-MS m/z 220 [M+H]+

(2) Synthesis of
3-bromo-2-methoxy-4,6-dimethylpyridine

A mixture of 3-bromo-2-chloro-4,6-dimethylpyridine (2.97 g), a 28% sodium methoxide methanol solution (11.0 mL) and DMF (30 mL) was stirred at 80° C. for 36 hours. Water was added to the reaction mixture and was extracted with diethyl ether. The organic layer was concentrated under reduced pressure and the residue was purified by silica gel column chromatography (ethyl acetate/n-heptane, 0% to 10%) to obtain the title compound (2.33 g).

$^1$H-NMR (400 MHz, CDCl$_3$) δ (ppm): 2.33-2.34 (m, 3H), 2.36-2.38 (m, 3H), 3.98 (s, 3H), 6.61-6.64 (m, 1H).

ESI-MS m/z 216 [M+H]$^+$

Production Example 3

Synthesis of (2-methoxy-3,5-dimethylpyridin-4-yl)boronic acid

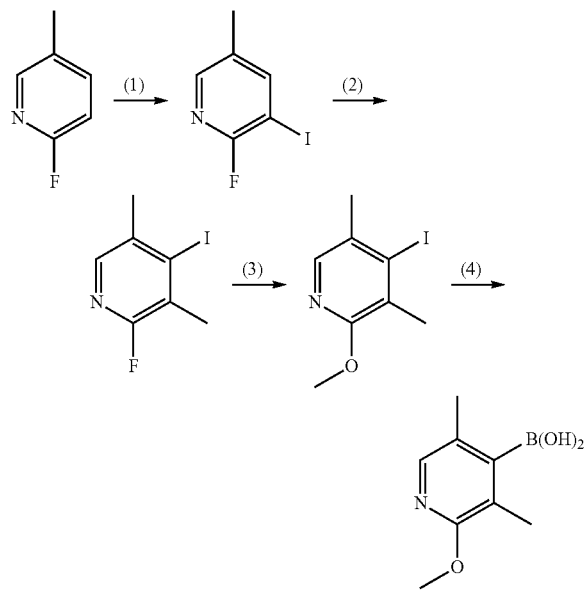

(1) Synthesis of 2-fluoro-3-iodo-5-methylpyridine

A 2.69 M n-butyllithium hexane solution (224 mL) was added dropwise to a mixture of diisopropylamine (92 mL) and THF (1.2 L) at −18° C. under a nitrogen atmosphere. Upon completion of the dropwise addition, the mixture was stirred while raising the temperature to −5° C. over a period of 20 minutes. The reaction mixture was cooled to −73° C., and then a solution of 2-fluoro-5-methylpyridine (61 g) in THF (240 mL) was added dropwise thereto. The reaction mixture was stirred at −75° C. for 3.5 hours. A solution of iodine (139 g) in THF (24 mL) was added dropwise to the reaction mixture. The reaction mixture was stirred at −75° C. for 1 hour and 55 minutes. Upon completion of the reaction, water (220 mL) was added to the reaction mixture at the same temperature. The mixture was stirred for 5 minutes at the same temperature. The reaction mixture was warmed to room temperature, and then water (1.2 L) was added. An aqueous sodium thiosulfate pentahydrate (136 g) solution (300 mL) and water (300 mL) were added to the mixture, and the resultant was stirred for 10 minutes. The mixture was extracted with MTBE (1.2 L). The organic layer was washed with brine (500 mL). The combined aqueous layer was extracted with MTBE (1 L). The combined organic layer was dried over anhydrous magnesium sulfate. The desiccant was filtered out, and the filtrate was concentrated under reduced pressure. After adding n-heptane to the residue, the mixture was cooled. The precipitated solid was filtered out, and then was rinsed with n-heptane. The filtrate was cooled and the precipitated solid was filtered out. This procedure was repeated 5 times to obtain the title compound (109.69 g).

$^1$H-NMR (400 MHz, CDCl$_3$) δ (ppm): 2.29-2.31 (m, 3H), 7.93-8.14 (m, 2H).

ESI-MS m/z 238 [M+H]$^+$ (2) Synthesis of 2-fluoro-4-iodo-3,5-dimethylpyridine

A 2.69 M n-butyllithium hexane solution (215 mL) was added dropwise to a mixture of diisopropylamine (88 mL) and THF (1.2 L) at −18° C. under a nitrogen atmosphere. Upon completion of the dropwise addition, the mixture was stirred while raising the temperature to −5° C. over a period of 30 minutes. The reaction mixture was cooled to −72° C., and then a solution of 2-fluoro-3-iodo-5-methylpyridine (109.69 g) in THF (240 mL) was added dropwise thereto. The reaction mixture was stirred at −74° C. for 1.5 hours. A solution of methyl iodide (36 mL) in THF (160 mL) was added dropwise to the reaction mixture. The reaction mixture was stirred at −70° C. to −74° C. for 2 hours. Upon completion of the reaction, water (200 mL) was added to the reaction mixture at the same temperature. The mixture was stirred for 2 minutes at the same temperature. The reaction mixture was warmed to room temperature, and then water (1.2 L) was added. The obtained mixture was stirred for 3 minutes, water (300 mL) was further added thereto. The mixture was extracted with MTBE (1.2 L). The organic layer was washed with brine (500 mL). The combined aqueous layer was extracted with MTBE (1 L). The combined organic layer was dried over anhydrous magnesium sulfate. The desiccant was filtered out, and the filtrate was concentrated under reduced pressure. After adding n-heptane (100 mL) to the residue, the mixture was cooled. The precipitated solid was filtered out, and then was rinsed with n-heptane. The filtrate was cooled and the precipitated solid was filtered out. This procedure was repeated 2 times to obtain the title compound (86.9 g).

$^1$H-NMR (400 MHz, CDCl$_3$) δ (ppm): 2.39-2.40 (m, 6H), 7.80-7.82 (m, 1H).

ESI-MS m/z 252 [M+H]$^+$ (3) Synthesis of 4-iodo-2-methoxy-3,5-dimethylpyridine

To a solution of 2-fluoro-4-iodo-3,5-dimethylpyridine (97.4 g) in THF (954 mL) there was added a 28% sodium methoxide methanol solution (185 mL) at 20° C. The mixture was stirred at 55° C. to 65° C. for 2 hours. After cooling the reaction mixture, MTBE (1 L) and water (1 L) were added for separation. The organic layer was washed with brine. The combined aqueous layer was extracted with MTBE (500 mL×2). The combined organic layer was dried over anhydrous magnesium sulfate. The desiccant was filtered out, and the filtrate was concentrated under reduced pressure. After adding n-heptane (50 mL) to the residue, the mixture was stirred at 0° C. for 1 hour. The precipitated solid was filtered out. The solid was rinsed with cooled n-heptane (10 mL) to obtain the title compound (42.6 g). The filtrate was concentrated under reduced pressure. After adding n-heptane (5 mL) to the residue, the mixture was stirred at 0° C. for 30 minutes. The precipitated solid was filtered out.

The solid was rinsed with cooled n-heptane (2 mL) to obtain the title compound (20.2 g). The filtrate was concentrated under reduced pressure. After adding n-heptane (5 mL) to the residue, the mixture was stirred at 0° C. for 30 minutes. The precipitated solid was filtered out. The solid was rinsed with cooled n-heptane (2 mL) to obtain the title compound (10.7 g). This was combined to obtain the title compound (73.5 g).

$^1$H-NMR (400 MHz, CDCl$_3$) δ (ppm): 2.33-2.34 (m, 3H), 2.36-2.38 (m, 3H), 3.92 (s, 3H), 7.76 (s, 1H).

ESI-MS m/z 264 [M+H]$^+$ (4) Synthesis of (2-methoxy-3,5-dimethylpyridin-4-yl)boronic acid A 2.69 M n-butyllithium hexane solution (6.5 mL) was added dropwise to a mixture of 4-iodo-2-methoxy-3,5-dimethylpyridine (2.0 g) and THF (40 mL) at −78° C. over a period of 10 minutes. The mixture was stirred at −78° C. for 20 minutes. Triisopropyl borate (5.26 mL) was added dropwise to the mixture over a period of 5 minutes. The mixture was stirred while being warmed to 20° C. over a period of 1.5 hours. Water was added to the reaction mixture and the resultant was extracted with ethyl acetate. The obtained aqueous layer was neutralized with citric acid, and was extracted with ethyl acetate. The combined organic layer was dried over anhydrous magnesium sulfate. The desiccant was filtered out, and the filtrate was concentrated under reduced pressure. MTBE was added to the residue for trituration. The precipitated solid was filtered out. This solid was used as first crystals. The filtrate was concentrated under reduced pressure. MTBE was added to the residue for trituration. The precipitated title compound (551 mg) was filtered out. The first crystals were suspended in ethyl acetate. A small amount of MTBE was added for trituration. The precipitated title compound (553.3 mg) was filtered out. The filtrate was concentrated under reduced pressure. MTBE was added to the residue for trituration. The precipitated title compound (121.1 mg) was filtered out. This was combined to obtain the title compound (1.23 g).

$^1$H-NMR (400 MHz, CDCl$_3$) δ (ppm): 2.19-2.20 (m, 3H), 2.23-2.24 (m, 3H), 3.91 (s, 3H), 4.94 (brs, 2H), 7.74 (s, 1H).

ESI-MS m/z 182 [M+H]$^+$

Production Example 4

Synthesis of ethyl 1-(3-methyltetrahydro-2H-pyran-4-yl)-5-[2-nitro-4-(4,4,5,5-tetramethyl-1,3,2-dioxaborolan-2-yl)phenyl]-1H-pyrazole-4-carboxylate

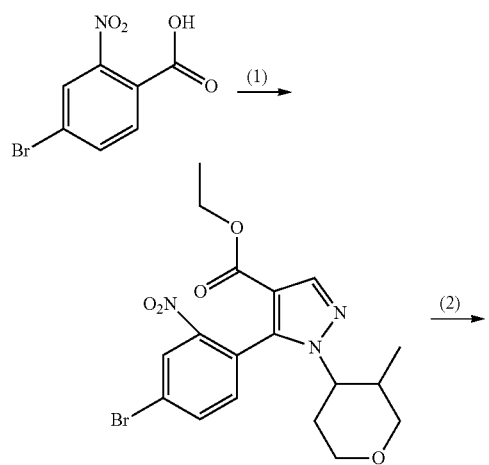

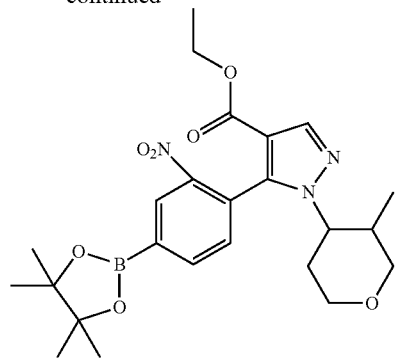

(1) Synthesis of ethyl 5-(4-bromo-2-nitrophenyl)-1-(3-methyltetrahydro-2H-pyran-4-yl)-1H-pyrazole-4-carboxylate Thionyl chloride (1.9 mL) was added to a mixture of 4-bromo-2-nitrobenzoic acid (6 g) and acetonitrile (60 mL), and the mixture was stirred at 50° C. for 2 hours. Triethylamine (6.8 mL) and ethyl 3-dimethylaminoacrylate (3.9 mL) were added dropwise to the reaction mixture under ice-cooling. After stirring at room temperature for 2 hours, the reaction mixture was filtered. The filtrate was concentrated under reduced pressure. Ethyl acetate was added to the residue, the obtained suspension was filtered and the filtrate was concentrated under reduced pressure. This procedure was repeated two more times. The obtained filtrate was concentrated under reduced pressure to obtain ethyl 2-(4-bromo-2-nitrobenzoyl)-3-(dimethylamino)acrylate (11 g) as a crude product. This ethyl 2-(4-bromo-2-nitrobenzoyl)-3-(dimethylamino)acrylate (2.95 g) was dissolved in acetonitrile (20 mL). To this solution there were added (3-methyltetrahydro-2H-pyran-4-yl)hydrazine hydrochloride (1.3 g) (synthesized according to Giovannini, Riccardo et al., PCT Int. Appl. (2009), WO2009121919, Examples 8CA, 8CB) and water (2 mL). The reaction mixture was stirred overnight at room temperature and then stirred at 90° C. for 2 hours. The reaction mixture was cooled to room temperature and then concentrated under reduced pressure. Ethyl acetate and water were added to the residue, and the organic layer was separated off. The aqueous layer was extracted with ethyl acetate. The combined organic layer was dried over anhydrous magnesium sulfate and the desiccant was filtered out. The filtrate was concentrated under reduced pressure. The residue was purified by silica gel column chromatography (ethyl acetate/n-heptane, 10-100%) to obtain the title compound (0.66 g).

ESI-MS m/z 460 [M+Na]$^+$ (2) Synthesis of ethyl 1-(3-methyltetrahydro-2H-pyran-4-yl)-5-[2-nitro-4-(4,4,5,5-tetramethyl-1,3,2-dioxaborolan-2-yl)phenyl]-1H-pyrazole-4-carboxylate Ethyl 5-(4-bromo-2-nitrophenyl)-1-(3-methyltetrahydro-2H-pyran-4-yl)-1H-pyrazole-4-carboxylate (398 mg), bis(pinacolato)diboron (277 mg), potassium acetate (267 mg) and Pd(dppf)Cl$_2$.DCM complex (37.1 mg) were added to 1,4-dioxane (10 mL). This mixture was stirred for 2 hours at 90° C. under a nitrogen atmosphere. The reaction mixture was cooled to room temperature and then filtered with Celite. Ethyl acetate (50 mL) and water (50 mL) were added to the filtrate, and the organic layer and aqueous layer were separated. The aqueous layer was extracted with ethyl acetate (50 mL). The combined organic layer was washed with brine (50 mL), dried over anhydrous magnesium sulfate, and the desiccant was filtered out. The filtrate was concentrated under reduced pressure. The residue was purified by silica gel column chromatography (ethyl acetate/n-heptane, 10-80%) to obtain the title compound (441.0 mg) as a crude product.

ESI-MS m/z 405 [M-C$_6$H$_{10}$+H]$^+$

The structure of 4,4,5,5-tetramethyl-1,3,2-dioxaborolane of the title compound was decomposed and the molecular weight of the boronic acid (B(OH)$_2$) compound was detected.

Production Example 5

Synthesis of (1,4-dioxaspiro[4.5]decan-8-yl)hydrazine hydrochloride

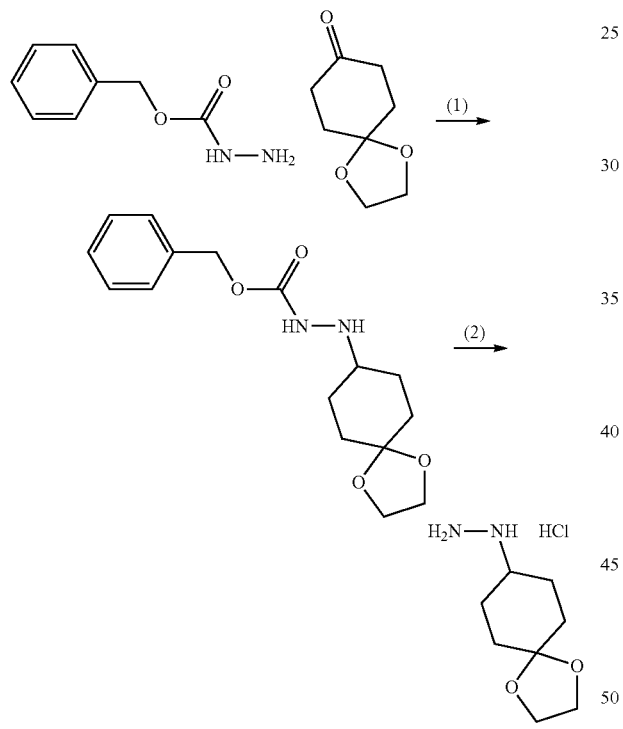

(1) Synthesis of benzyl 2-(1,4-dioxaspiro[4.5]decan-8-yl)hydrazine carboxylate

To a solution of 1,4-cyclohexanedione monoethyleneketal (CAS No. 4746-97-8, 5.0 g) in methanol (100 mL) there was added benzyl carbazate (CAS No. 5331-43-1, 5.32 g), and the mixture was stirred at room temperature for 1 hour. The reaction mixture was then concentrated. The obtained residue was dissolved in THF and again concentrated. Sodium borohydride (2.42 g) was added to a solution of the obtained residue in THF (80 mL) at room temperature, and then the reaction mixture was stirred for 15 minutes at the same temperature. After the reaction mixture was ice-cooled, methanol (10 mL) was added dropwise to the reaction mixture over a period of 30 minutes, the reaction mixture was stirred at room temperature for 1.5 hours. Next, water (15 mL) was added dropwise to the reaction mixture over a period of 15 minutes, and the reaction mixture was stirred for 5 minutes at room temperature. Water (15 mL) was further added to the reaction mixture, and the reaction mixture was stirred at room temperature for 10 minutes. The THF was distilled off from the reaction mixture under reduced pressure. Ethyl acetate was added to the obtained residue, and after stirring the mixture for 15 minutes, the organic layer was separated. The obtained organic layer was washed with brine, dried over anhydrous magnesium sulfate. The desiccant was filtered out and the filtrate was concentrated under reduced pressure. The obtained residue was purified by silica gel column chromatography (ethyl acetate/n-heptane, 50%) and triturated with a mixed solvent of MTBE and hexane (1:1). The obtained powder was filtered and dried under reduced pressure to obtain the title compound (7.52 g).

$^1$H-NMR (400 MHz, CD$_3$OD) δ (ppm): 1.40-1.55 (m, 4H), 1.70-1.85 (m, 4H), 2.84 (brs, 1H), 3.90 (s, 4H), 5.10 (s, 2H), 7.24-7.40 (m, 5H).

ESI-MS m/z 329 [M+Na]$^+$ (2) Synthesis of (1,4-dioxaspiro[4.5]decan-8-yl)hydrazine hydrochloride To a suspension of benzyl 2-(1,4-dioxaspiro[4.5]decan-8-yl)hydrazine carboxylate (4.0 g) in ethanol (40 mL)-chloroform (3.16 mL) there was added 10% palladium on carbon (water content: 50%, 400 mg), and the mixture was stirred for 23.5 hours at room temperature under a hydrogen atmosphere. The palladium on carbon was filtered out from the reaction mixture. The filtrate was concentrated under reduced pressure to obtain the title compound (3.06 g).

$^1$H-NMR (400 MHz, CD$_3$OD) δ (ppm): 1.57-1.90 (m, 8H), 3.06 (brs, 1H), 3.91 (s, 4H).

Example 1a

Synthesis of (+)-7-(6-methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((+)-cis)

Example 1b (−)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((−)-cis)

Example 1c (+)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((+)-trans)

Example 1d (−)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((−)-trans)

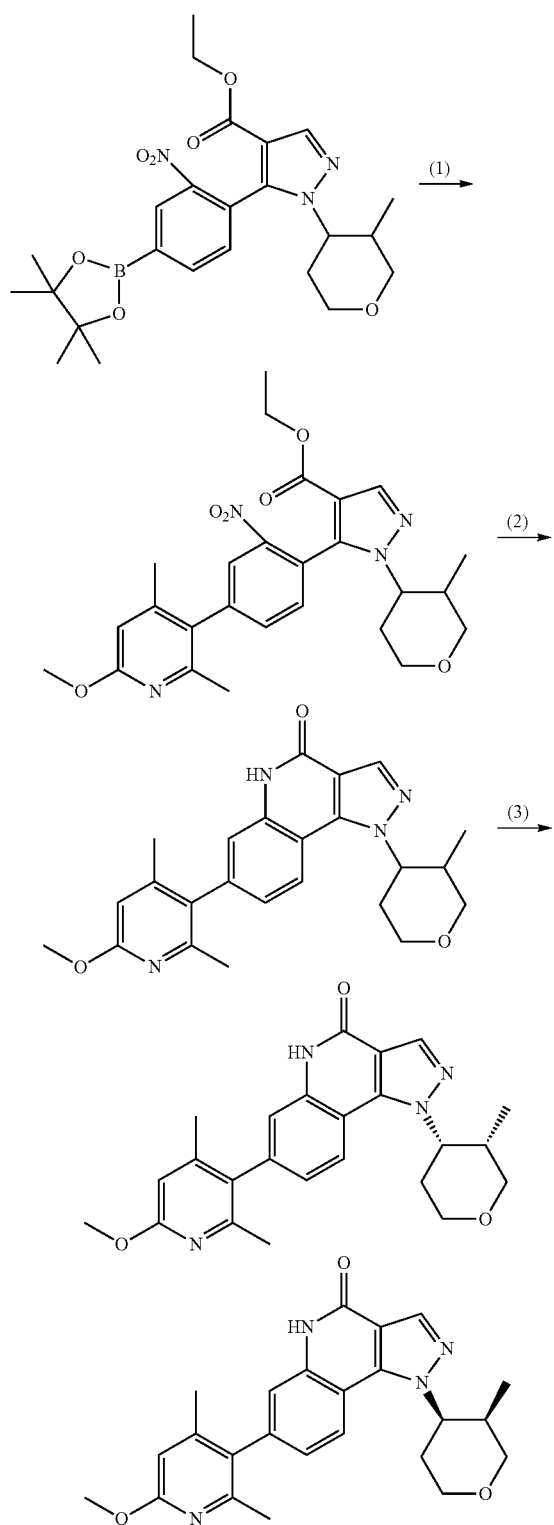

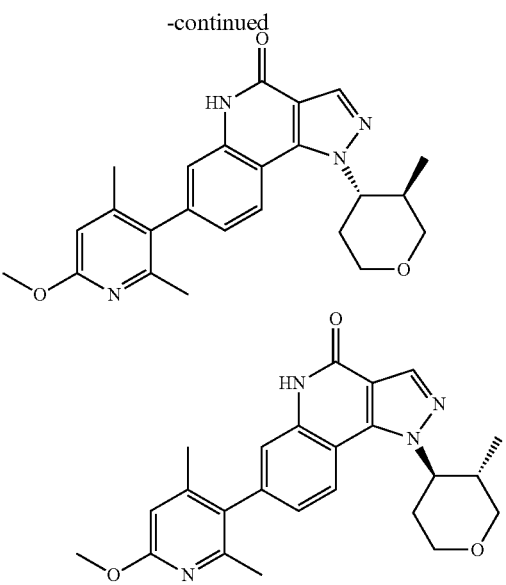

(1) Synthesis of ethyl 5-[4-(6-methoxy-2,4-dimethylpyridin-3-yl)-2-nitrophenyl]-1-(3-methyltetrahydro-2H-pyran-4-yl)-1H-pyrazole-4-carboxylate The ethyl 1-(3-methyltetrahydro-2H-pyran-4-yl)-5-[2-nitro-4-(4,4,5,5-tetramethyl-1,3,2-dioxaborolan-2-yl)phenyl]-1H-pyrazole-4-carboxylate obtained in Production Example 4 (220 mg), the 3-bromo-6-methoxy-2,4-dimethylpyridine obtained in Production Example 1 (196 mg) and sodium carbonate (144 mg) were added to a liquid mixture of 1,4-dioxane (3.9 mL) and water (0.8 mL) at 20° C. After adding Pd(PPh$_3$)$_4$ (52.4 mg) to the liquid mixture, it was stirred at 110° C. for 2 hours. The reaction mixture was cooled to room temperature, and then ethyl acetate was added to the reaction mixture. The organic layer and aqueous layer were separated. The aqueous layer was extracted with ethyl acetate (10 mL×2). The combined organic layer was washed with brine (10 mL), dried over anhydrous magnesium sulfate and filtered. The filtrate was concentrated under reduced pressure. The residue was purified by silica gel column chromatography (ethyl acetate/n-heptane, 30-70%) to obtain the title compound (137 mg).
ESI-MS m/z 495 [M+H]$^+$ (2) Synthesis of 7-(6-methoxy-2,4-dimethylpyridin-3-yl)-1-(3-methyltetrahydro-2H-pyran-4-yl)-1H-pyrazolo[4,3-c]quinoline-4(5H)-one Ethyl 5-[4-(6-methoxy-2,4-dimethylpyridin-3-yl)-2-nitrophenyl]-1-(3-methyltetrahydro-2H-pyran-4-yl)-1H-pyrazole-4-carboxylate (135 mg) was dissolved in acetic acid (1.6 mL). Iron powder (45.7 mg) was added to the solution at 20° C. The reaction mixture was stirred at 90° C. for 4 hours. Ethyl acetate (10 mL) was added to the reaction mixture for dilution, and an aqueous sodium hydrogen carbonate solution was added for neutralization. The organic layer and aqueous layer were separated. The aqueous layer was extracted with ethyl acetate (25 mL×2). The combined organic layer was washed with brine (10 mL), dried over anhydrous magnesium sulfate and the desiccant was filtered out. The filtrate was concentrated under reduced pressure.

The residue was purified by silica gel column chromatography (ethyl acetate/n-heptane, 50-100%) to obtain the title compound (76 mg).
ESI-MS m/z 419 [M+H]+

(3) Synthesis of (+)-7-(6-methoxy-2,4-dimethylpyridin-3-yl)-1-((3R,4R)-3-methyltetrahydro-2H-pyran-4-yl)-1H-pyrazolo[4,3-c]quinoline-4(5H)-one, (−)-7-(6-methoxy-2,4-dimethylpyridin-3-yl)-1-((3R*,4R*)-3-methyltetrahydro-2H-pyran-4-yl)-1H-pyrazolo[4,3-c]quinoline-4(5H)-one, (+)-7-(6-methoxy-2,4-dimethylpyridin-3-yl)-1-((3R*,4S*)-3-methyltetrahydro-2H-pyran-4-yl)-1H-pyrazolo[4,3-c]quinoline-4(5H)-one and (−)-7-(6-methoxy-2,4-dimethylpyridin-3-yl)-1-((3R*,4S*)-3-methyltetrahydro-2H-pyran-4-yl)-1H-pyrazolo[4,3-c]quinoline-4(5H)-one 7-(6-Methoxy-2,4-dimethylpyridin-3-yl)-1-(3-methyltetrahydro-2H-pyran-4-yl)-1H-pyrazolo[4,3-c]quinoline-4(5H)-one (12 mg) was dissolved in ethanol (10 mL). The solution was purified by chiral HPLC conditions (column: CHIRALPAK® IA by Daicel, moving phase: ethanol). A mixture (8 mg) of (+)-7-(6-methoxy-2,4-dimethylpyridin-3-yl)-1-((3R*,4S*)-3-methyltetrahydro-2H-pyran-4-yl)-1H-pyrazolo[4,3-c]quinoline-4(5H)-one (trans) and (−)-7-(6-methoxy-2,4-dimethylpyridin-3-yl)-1-((3R*,4S*)-3-methyltetrahydro-2H-pyran-4-yl)-1H-pyrazolo[4,3-c]quinoline-4(5H)-one (trans) was obtained as the first fraction. (+)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((+)-cis) (3 mg) was obtained as the second fraction. (−)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((−)-cis) (3 mg) was obtained as the third fraction. The mixture of the trans-isomers (8 mg) was separated under chiral HPLC conditions (column: CHIRALCEL® OD-H by Daicel, mobile phase: ethanol). (−)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((−)-trans) (1 mg) was obtained as the first fraction, and (+)-7-(6-methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((+)-trans) (1 mg) was obtained as the second fraction.

(+)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((+)-cis)

1H-NMR (400 MHz, CDCl3) δ (ppm): 0.93 (d, J=6.6 Hz, 3H), 2.01-2.09 (m, 4H), 2.21-2.23 (m, 3H), 2.45-2.54 (m, 1H), 2.93-3.07 (m, 1H), 3.63-3.73 (m, 1H), 3.82-3.89 (m, 1H), 3.97 (s, 3H), 3.98-4.03 (m, 1H), 4.23-4.31 (m, 1H), 5.18-5.26 (m, 1H), 6.55 (s, 1H), 7.12 (dd, J=8.2 Hz, 1.6 Hz, 1H), 7.18-7.31 (m, 1H), 8.01 (d, J=8.2 Hz, 1H), 8.30 (s, 1H), 10.15 (brs, 1H).
ESI-MS m/z 419 [M+H]+
Column: CHIRALPAK® IA by Daicel, mobile phase: ethanol, retention time: 17.1 minutes.

(−)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((−)-cis)

Column: CHIRALPAK® IA by Daicel, mobile phase: ethanol, retention time: 20.4 minutes.

The 1H-NMR data for the (−)-cis isomer was identical to the 1H-NMR data for the corresponding (+)-cis isomer.

(−)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((−)-trans)

1H-NMR (400 MHz, CDCl3) δ (ppm): 0.76 (d, J=6.6 Hz, 3H), 2.02-2.05 (m, 3H), 2.10-2.18 (m, 1H), 2.21-2.24 (m, 3H), 2.34-2.48 (m, 1H), 2.79-2.92 (m, 1H), 3.31 (t, J=11.5 Hz, 1H), 3.66-3.75 (m, 1H), 3.97 (s, 3H), 4.13 (dd, J=11.9 Hz, 4.5 Hz, 1H), 4.18-4.26 (m, 1H), 4.68 (td, J=10.9 Hz, 4.3 Hz, 1H), 6.55 (s, 1H), 7.12 (dd, J=8.2 Hz, 1.6 Hz, 1H), 7.26 (d, J=1.6 Hz, 1H), 8.08 (d, J=8.2 Hz, 1H), 8.36 (s, 1H), 10.57 (brs, 1H).
ESI-MS m/z 419 [M+H]+
Column: CHIRALCEL® OD-H by Daicel, moving phase: ethanol, retention time: 13.3 minutes.

(+)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((+)-trans)

Column: CHIRALCEL® OD-H by Daicel, mobile phase: ethanol, retention time: 19.7 minutes.
The 1H-NMR data for the (+)-trans isomer was identical to the 1H-NMR data for the corresponding (−)-trans isomer.

Example 2a

Synthesis of (+)-7-(2-methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((+)-trans)

Example 2b (−)-7-(2-Methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((−)-cis)

Example 2c (+)-7-(2-Methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((+)-cis)

Example 2d (−)-7-(2-Methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((−)-trans)

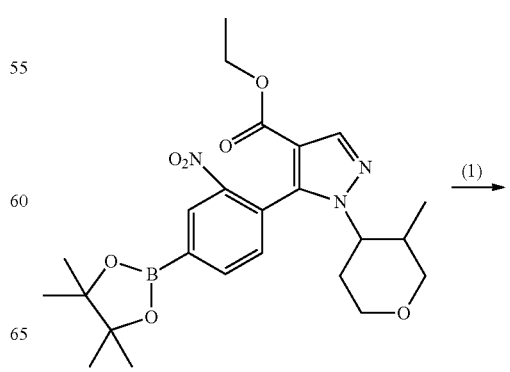

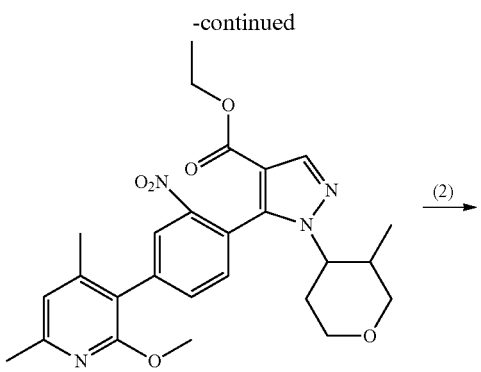

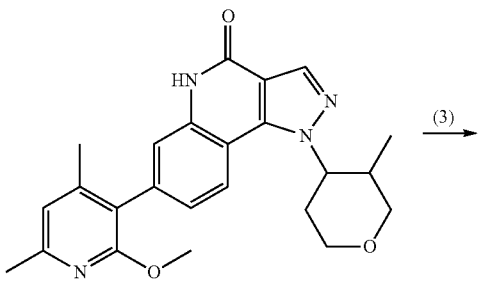

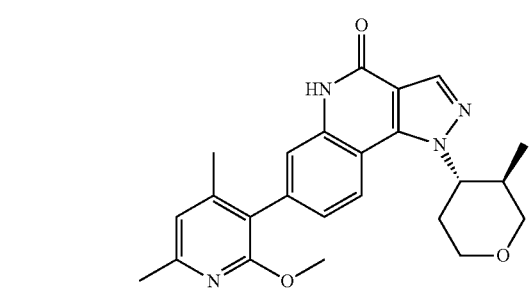

(1) Synthesis of ethyl 5-[4-(2-methoxy-4,6-dimethylpyridin-3-yl)-2-nitrophenyl]-1-(3-methyltetrahydro-2H-pyran-4-yl)-1H-pyrazole-4-carboxylate The ethyl 1-(3-methyltetrahydro-2H-pyran-4-yl)-5-[2-nitro-4-(4,4,5,5-tetramethyl-1,3,2-dioxaborolan-2-yl)phenyl]-1H-pyrazole-4-carboxylate obtained in Production Example 4 (220 mg), the 3-bromo-2-methoxy-4,6-dimethylpyridine obtained in Production Example 2 (196 mg) and sodium carbonate (144 mg) were added to a liquid mixture of 1,4-dioxane (3.9 mL) and water (0.8 mL) at 20° C. After adding Pd(PPh$_3$)$_4$ (52.4 mg) to the liquid mixture, it was stirred at 110° C. for 2 hours. The reaction mixture was cooled to room temperature, and then ethyl acetate was added to the reaction mixture. The organic layer and aqueous layer were separated. The aqueous layer was extracted with ethyl acetate (10 mL×2). The combined organic layer was washed with brine (10 mL), dried over anhydrous magnesium sulfate and the desiccant was filtered out. The filtrate was concentrated under reduced pressure. The residue was purified by silica gel column chromatography (ethyl acetate/n-heptane, 30-70%) to obtain the title compound (133 mg).

ESI-MS m/z 495 [M+H]$^+$ (2) Synthesis of 7-(2-methoxy-4,6-dimethylpyridin-3-yl)-1-(3-methyltetrahydro-2H-pyran-4-yl)-1H-pyrazolo[4,3-c]quinoline-4(5H)-one Ethyl 5-[4-(2-methoxy-4,6-dimethylpyridin-3-yl)-2-nitrophenyl]-1-(3-methyltetrahydro-2H-pyran-4-yl)-1H-pyrazole-4-carboxylate (133 mg) was dissolved in acetic acid (1.5 mL). Iron powder (45.1 mg) was added to the solution at 20° C. The reaction mixture was stirred at 90° C. for 4 hours. Ethyl acetate (10 mL) was added to the reaction mixture for dilution, and an aqueous sodium hydrogen carbonate solution was added for neutralization. The organic layer and aqueous layer were separated. The aqueous layer was extracted with ethyl acetate (25 mL×2). The combined organic layer was washed with brine (10 mL), dried over anhydrous magnesium sulfate, and the desiccant was filtered out. The filtrate was concentrated under reduced pressure. The residue was purified by silica gel column chromatography (ethyl acetate/n-heptane, 50-100%) to obtain the title compound (73 mg).

ESI-MS m/z 419 [M+H]$^+$ (3) Synthesis of (+)-7-(2-methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((+)-trans), (−)-7-(2-methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((−)-cis), (−)-7-(2-methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((−)-trans) and (+)-7-(2-methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((+)-cis)

7-(2-Methoxy-4,6-dimethylpyridin-3-yl)-1-(3-methyltetrahydro-2H-pyran-4-yl)-1H-pyrazolo[4,3-c]quinoline-4(5H)-one (30 mg) was dissolved in ethanol (5 mL). The solution was purified by chiral HPLC conditions (column: CHIRALPAK® AD-H by Daicel, mobile phase: ethanol). A mixture (14 mg) of (+)-7-(2-methoxy-4,6-dimethylpyridin-3-yl)-1-((3R*,4R*)-3-methyltetrahydro-2H-pyran-4-yl)-1H-pyrazolo[4,3-c]quinoline-4(5H)-one (cis) and (−)-7-(2-methoxy-4,6-dimethylpyridin-3-yl)-1-((3R*,4 S*)-3-methyltetrahydro-2H-pyran-4-yl)-1H-pyrazolo[4,3-c]quinoline-4(5H)-one (trans) was obtained as the first fraction. (+)-7-(2-Methoxy-4,6-dimethylpyridin-3-yl)-1-((3R*,4 S*)-3-methyltetrahydro-2H-pyran-4-yl)-1H-pyrazolo[4,3-c]quinoline-4(5H)-one ((+)-trans) (3 mg) was obtained as the second fraction. (−)-7-(2-Methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((−)-cis) (3 mg) was obtained as the third fraction. The mixture (14 mg) described above was separated under chiral HPLC conditions (column: CHIRALCEL® OD-H by Daicel, mobile phase: ethanol/n-hexane (70%)). (−)-7-(2-Methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((−)-trans) (5 mg) was obtained as the first fraction, and (+)-7-(2-methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((+)-cis) (5 mg) was obtained as the second fraction.

(+)-7-(2-Methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((+)-trans)

$^1$H-NMR (400 MHz, CDCl$_3$) δ (ppm): 0.75 (d, J=6.6 Hz, 3H), 2.11 (s, 3H), 2.11-2.19 (m, 1H), 2.29-2.49 (m, 1H), 2.48 (s, 3H), 2.78-2.89 (m, 1H), 3.29 (t, J=11.3 Hz, 1H), 3.64-3.71 (m, 1H), 3.86 (s, 3H), 4.08-4.15 (m, 1H), 4.17-4.25 (m, 1H), 4.62-4.71 (m, 1H), 6.74 (s, 1H), 7.18 (d, J=8.0 Hz, 1H), 7.27 (s, 1H), 8.06 (d, J=8.0 Hz, 1H), 8.34 (s, 1H), 10.03 (brs, 1H).
ESI-MS m/z 419 [M+H]$^+$
Column: CHIRALPAK® AD-H by Daicel, mobile phase: ethanol, retention time: 23.8 minutes.

(−)-7-(2-Methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((−)-cis)

ESI-MS m/z 419[M+H]$^+$
Column: CHIRALPAK® AD-H by Daicel, mobile phase: ethanol, retention time: 31.4 minutes.
The $^1$H-NMR data for the (−)-cis isomer was identical to the $^1$H-NMR data for the corresponding (+)-cis isomer.

(−)-7-(2-Methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((−)-trans)

Column: CHIRALCEL® OD-H by Daicel, mobile phase: ethanol/n-hexane (70%), retention time: 13 minutes.
The $^1$H-NMR data for the (−)-trans isomer was identical to the $^1$H-NMR data for the corresponding (+)-trans isomer.

(+)-7-(2-Methoxy-4,6-dimethylpyridin-3-yl)-1-((3R*,4R*)-3-methyltetrahydro-2H-pyran-4-yl)-1H-pyrazolo[4,3-c]quinoline-4(5H)-one ((+)-cis)

$^1$H-NMR (400 MHz, CDCl$_3$) δ (ppm): 0.90 (d, J=7.2 Hz, 3H), 2.00-2.09 (m, 1H), 2.10 (s, 3H), 2.49 (s, 3H), 2.48-2.55 (m, 1H), 2.94-3.05 (m, 1H), 3.64-3.71 (m, 1H), 3.77-3.89 (m, 1H), 3.86 (s, 3H), 3.96-4.00 (m, 1H), 4.24-4.30 (m, 1H), 5.19-5.24 (m, 1H), 6.74 (s, 1H), 7.19 (dd, J=8.4 Hz, 1.6 Hz, 1H), 7.31 (d, J=1.6 Hz, 1H), 7.98 (d, J=8.4 Hz, 1H), 8.29 (s, 1H), 10.43 (brs, 1H).
Column: CHIRALCEL® OD-H by Daicel, moving phase: ethanol/n-hexane (70%), retention time: 14.9 minutes.

Example 3a

Synthesis of (−)-7-(2-methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((−)-cis)

Example 3b (+)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((+)-cis)

Example 4a (−)-7-(2-Methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((−)-trans)

Example 4b (+)-7-(2-Methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((+)-trans)

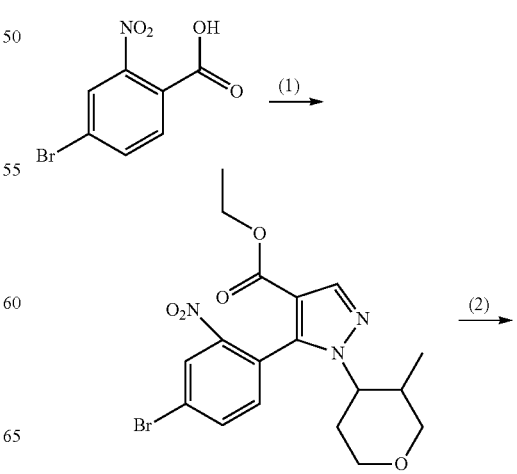

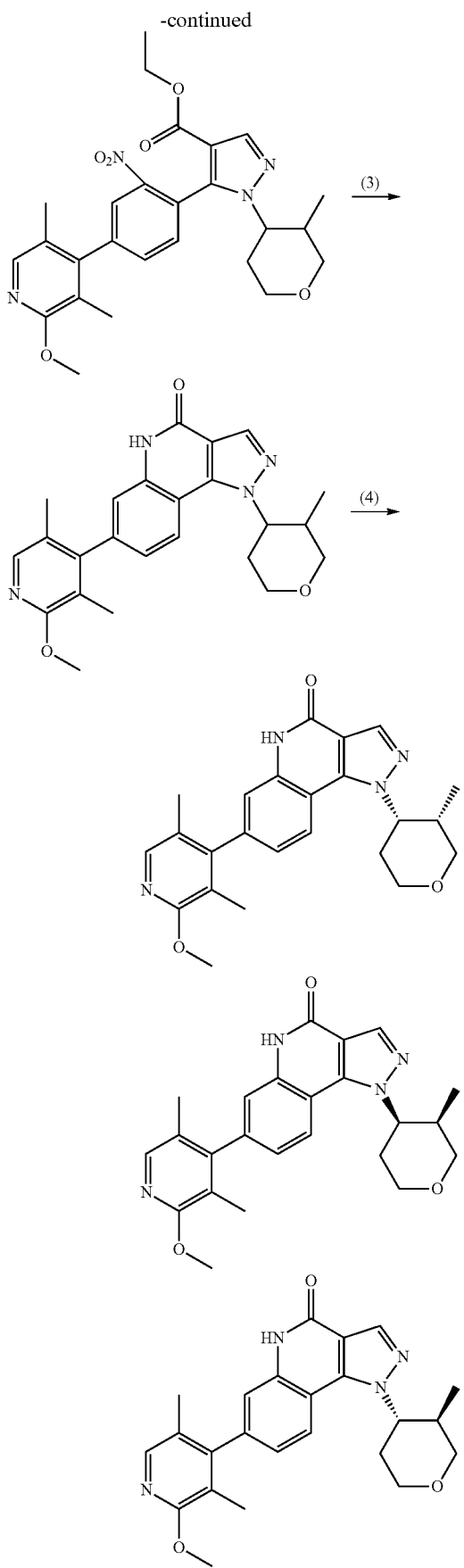

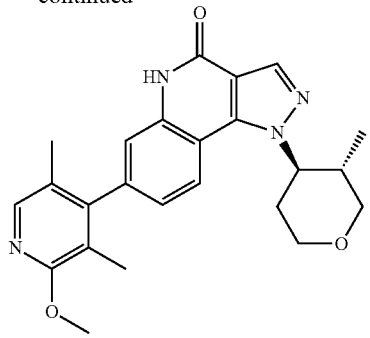

(1) Synthesis of ethyl 5-(4-bromo-2-nitrophenyl)-1-(3-methyltetrahydro-2H-pyran-4-yl)-1H-pyrazole-4-carboxylate 4-Bromo-2-nitrobenzoic acid (6 g) was dissolved in acetonitrile (60 mL). Thionyl chloride (1.9 mL) was added to the solution, and the mixture was stirred at 50° C. for 2 hours. Triethylamine (6.8 mL) was added dropwise to the reaction mixture under ice-cooling. Ethyl 3-dimethylaminoacrylate (3.9 mL) was also added dropwise to the reaction mixture. After stirring at room temperature for 2 hours, the reaction mixture was filtered. The filtrate was concentrated under reduced pressure. Ethyl acetate was added to the residue, and the produced suspension was filtered out. The filtrate was concentrated under reduced pressure. Ethyl acetate was added to the residue, the produced suspension was filtered out. The filtrate was concentrated under reduced pressure. Ethyl acetate was added to the residue, the produced suspension was filtered out. The filtrate was concentrated under reduced pressure to obtain ethyl 2-(4-bromo-2-nitrobenzoyl)-3-(dimethylamino)acrylate (11 g) as a crude product. The obtained ethyl 2-(4-bromo-2-nitrobenzoyl)-3-(dimethylamino)acrylate (2.95 g) was dissolved in acetonitrile (20 mL). (3-Methyltetrahydro-2H-pyran-4-yl)hydrazine hydrochloride (1.3 g) (synthesized according to Giovannini, Riccardo et al., PCT Int. Appl. (2009), WO2009121919, Examples 8CA, 8CB) and water (2 mL) were added to the solution. The reaction mixture was stirred overnight at room temperature and then stirred at 90° C. for 2 hours. The reaction mixture was cooled to room temperature and then concentrated under reduced pressure. Ethyl acetate and water were added to the residue. The organic layer was separated off. The aqueous layer was extracted with ethyl acetate. The combined organic layer was dried over anhydrous magnesium sulfate and the desiccant was filtered out. The filtrate was concentrated under reduced pressure. The residue was purified by silica gel column chromatography (ethyl acetate/n-heptane, 10-100%) to obtain the title compound (0.66 g).
ESI-MS m/z 460 [M+Na]+

(2) Synthesis of ethyl 5-[4-(2-methoxy-3,5-dimethylpyridin-4-yl)-2-nitrophenyl]-1-(3-methyltetrahydro-2H-pyran-4-yl)-1H-pyrazole-4-carboxylate After adding the (2-methoxy-3,5-dimethylpyridin-4-yl) boronic acid produced in Production Example 3 (265 mg), Pd(PPh₃)₄ (85 mg) and cesium carbonate (715 mg) to a liquid mixture of ethyl 5-(4-bromo-2-nitrophenyl)-1-(3-methyltetrahydro-2H-pyran-4-yl)-1H-pyrazole-4-carboxylate (320.8 mg), 1,4-dioxane (5 mL) and water (1.5 mL), the reaction mixture was stirred at 110° C. for 2 hours under a nitrogen atmosphere. After cooling the reaction mixture to room temperature, it was concentrated under reduced pressure. The residue was diluted with ethyl acetate and washed with water. The organic layer was dried over anhydrous magnesium sulfate, and the desiccant was filtered out. The filtrate was concentrated under reduced pressure. The residue was partially purified by silica gel column chromatography (ethyl acetate/n-heptane, 10-100%) to obtain the title compound (382.8 mg) as a crude product.

ESI-MS m/z 495 [M+H]$^+$ (3) Synthesis of 7-(2-methoxy-3,5-dimethylpyridin-4-yl)-1-(3-methyltetrahydro-2H-pyran-4-yl)-1H-pyrazolo[4,3-c]quinoline-4(5H)-one After dissolving ethyl 5-[4-(2-methoxy-3,5-dimethylpyridin-4-yl)-2-nitrophenyl]-1-(3-methyltetrahydro-2H-pyran-4-yl)-1H-pyrazole-4-carboxylate (112.3 mg) in acetic acid (2.5 mL) and water (0.25 mL), the mixture was stirred at 80° C. for 15 minutes under a nitrogen atmosphere. Iron powder (76 mg) was added at once to the reaction mixture, and after stirring the reaction mixture at 80° C. for 2 hours under a nitrogen atmosphere, it was stirred overnight at 90° C. under a nitrogen atmosphere. After cooling the reaction mixture to room temperature, it was diluted with ethyl acetate and concentrated under reduced pressure. The residue was diluted with chloroform and washed with a saturated aqueous sodium hydrogen carbonate solution. The organic layer was dried over anhydrous magnesium sulfate and the desiccant was filtered out. The filtrate was concentrated under reduced pressure. The residue was purified by short silica gel column chromatography (ethyl acetate) to obtain the title compound (91.2 mg).

$^1$H-NMR (400 MHz, CDCl$_3$) δ (ppm): 0.75-0.94 (m, 3H), 1.93-2.00 (m, 6H), 2.05-2.23 (m, 1H), 2.30-2.55 (m, 1H), 2.80-3.08 (m, 1H), 3.32 (t, J=12 Hz, 0.33H), 3.65-3.75 (m, 1H), 3.83-3.90 (m, 0.66H), 3.97-4.00 (m, 0.66H), 4.01 (s, 3H), 4.10-4.15 (m, 0.33H), 4.17-4.32 (m, 1H), 4.63-4.73 (m, 0.33H), 5.20-5.27 (m, 0.66H), 7.07-7.10 (m, 1H), 7.38 (s, 1H), 7.95 (s, 1H), 8.03-8.13 (m, 1H), 8.31 (s, 0.66H), 8.36 (s, 0.33H), 11.92-11.96 (m, 1H).

ESI-MS m/z 419 [M+H]$^+$ (4) Synthesis of (−)-7-(2-methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((−)-cis), (+)-7-(2-methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((+)-cis), (−)-7-(2-methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((−)-trans) and (+)-7-(2-methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((+)-trans)

7-(2-Methoxy-3,5-dimethylpyridin-4-yl)-1-(3-methyltetrahydro-2H-pyran-4-yl)-1H-pyrazolo[4,3-c]quinoline-4 (5H)-one (91.2 mg) was dissolved in 5% chloroform/ethanol (10.5 mL). The solution was purified by chiral HPLC conditions (column: CHIRALPAK® IA by Daicel, mobile phase: ethanol/n-hexane (50%)). A mixture (17.7 mg) of (−)-7-(2-methoxy-3,5-dimethylpyridin-4-yl)-1-((3R*,4S*)-3-methyltetrahydro-2H-pyran-4-yl)-1H-pyrazolo[4,3-c]quinoline-4(5H)-one and (+)-7-(2-methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((±)-trans) was obtained as the first fraction. (+)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((+)-cis) (25.9 mg) was obtained as the second fraction. (−)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((−)-cis) (25.9 mg) was obtained as the third fraction.

The mixture of (±)-trans-isomers (17.7 mg) was separated under chiral HPLC conditions (column: CHIRALPAK® IB by Daicel, mobile phase: ethanol/n-hexane (15%)). (−)-7-(2-Methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((−)-trans) (3.7 mg) was obtained as the first fraction, and (+)-7-(2-methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((+)-trans) (3.6 mg) was obtained as the second fraction.

(−)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((−)-cis)

$^1$H-NMR (400 MHz, CDCl$_3$) δ (ppm): 0.88-0.95 (m, 3H), 1.91-2.00 (m, 6H), 2.03-2.13 (m, 1H), 2.45-2.55 (m, 1H), 2.95-3.07 (m, 1H), 3.65-3.73 (m, 1H), 3.83-3.89 (m, 1H), 3.97-4.00 (m, 1H), 4.01 (s, 3H), 4.24-4.32 (m, 1H), 5.20-5.27 (m, 1H), 7.07-7.10 (m, 1H), 7.33 (s, 1H), 7.95 (s, 1H), 8.04 (d, J=8.4 Hz, 1H), 8.31 (s, 1H), 11.47 (brs, 1H).

ESI-MS m/z 419 [M+H]$^+$

Column: CHIRALPAK® IA by Daicel, mobile phase: ethanol/n-hexane (20%), retention time: 15 minutes.

(+)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((+)-cis)

Column: CHIRALPAK® IA by Daicel, mobile phase: ethanol/n-hexane (20%), retention time: 12.5 minutes.

The $^1$H-NMR data for the (+)-cis isomer was identical to the $^1$H-NMR data for the corresponding (−)-cis isomer.

(−)-7-(2-Methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((−)-trans)

$^1$H-NMR (400 MHz, CDCl$_3$) δ (ppm): 0.75-0.77 (m, 3H), 1.93-1.98 (m, 6H), 2.09-2.18 (m, 1H), 2.34-2.48 (m, 1H), 2.78-2.92 (m, 1H), 3.31 (t, J=11.4 Hz, 1H), 3.60-3.75 (m, 1H), 4.00 (s, 3H), 4.08-4.17 (m, 1H), 4.20-4.25 (m, 1H), 4.63-4.70 (m, 1H), 7.06-7.08 (m, 1H), 7.16-7.18 (m, 1H), 7.95 (s, 1H), 8.11 (d, J=11.4 Hz, 1H), 8.36 (s, 1H), 10.12 (brs, 1H).

ESI-MS m/z 419 [M+H]$^+$

Column: CHIRALPAK® IB by Daicel, mobile phase: ethanol/n-hexane (10%), retention time: 6.3 minutes.

(+)-7-(2-Methoxy-3,5-dimethylpyridin-4-yl)-1-((3R*,4S*)-3-methyltetrahydro-2H-pyran-4-yl)-1H-pyrazolo[4,3-c]quinoline-4(5H)-one ((+)-trans)

Column: CHIRALPAK® IB by Daicel, mobile phase: ethanol/n-hexane (10%), retention time: 7.8 minutes.

The $^1$H-NMR data for the (+)-trans isomer was identical to the $^1$H-NMR data for the corresponding (−)-trans isomer.

Example 5a
Synthesis of 7-(2-methoxy-3,5-dimethylpyridin-4-yl)-1-(cis-4-methoxycyclohexyl)-1H-pyrazolo[4,3-c]quinoline-4(5H)-one
Example 5b
Synthesis of 7-(2-methoxy-3,5-dimethylpyridin-4-yl)-1-(trans-4-methoxycyclohexyl)-1H-pyrazolo[4,3-c]quinoline-4(5H)-one
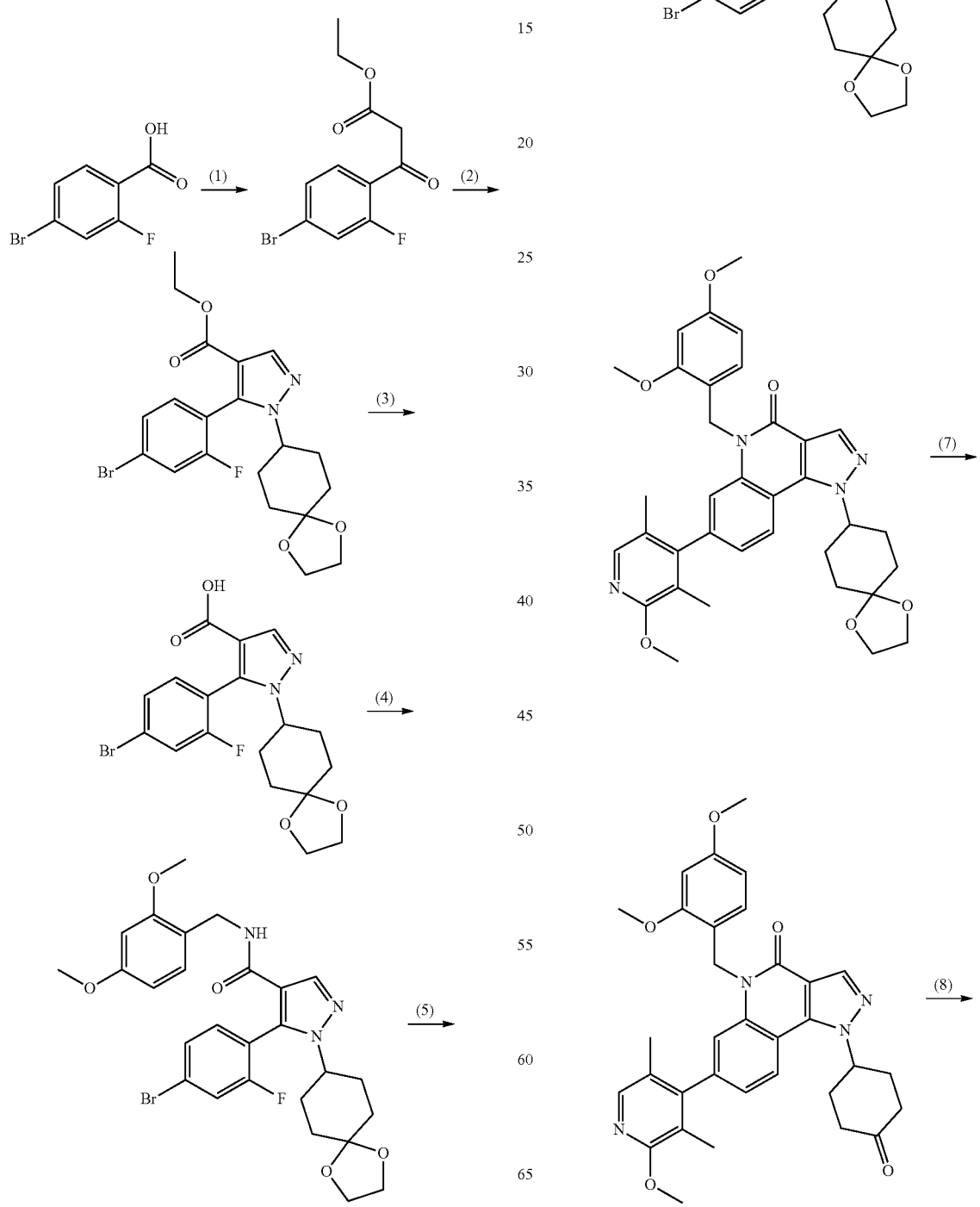

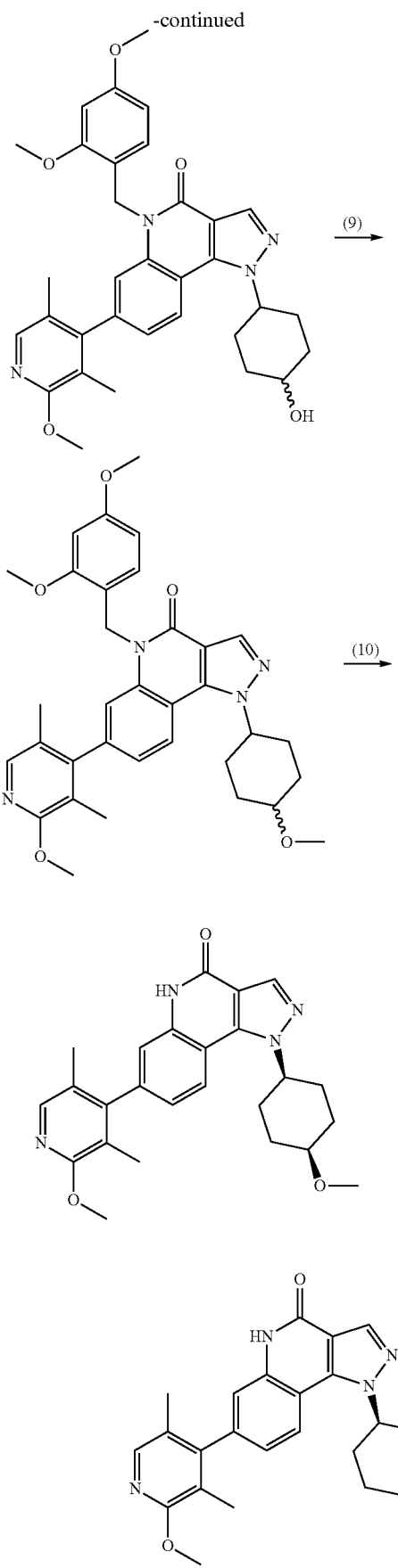

(1) Synthesis of ethyl 3-(4-bromo-2-fluorophenyl)-3-oxopropanoate

After adding CDI (8.88 g) to a suspension of 4-bromo-2-fluorobenzoic acid (CAS No. 112704-79-7) (10 g) in DCM (97 mL), the mixture was stirred at room temperature for 3.5 hours. This solution was used as "solution 1". TEA (15.9 mL) and magnesium chloride (10.9 g) were sequentially added to a suspension of potassium ethyl malonate (15.5 g) in acetonitrile (303 mL) in a separate flask, and the obtained mixture was stirred for 3 hours and 10 minutes at room temperature. The previously prepared "solution 1" was added dropwise to the reaction mixture over a period of 25 minutes, and then the reaction mixture was stirred overnight at room temperature. The reaction mixture was concentrated to half the amount under reduced pressure. The obtained residue was diluted with ethyl acetate (500 mL) and 5N hydrochloric acid (250 mL) was added under ice-cooling, and then the mixture was stirred for 1 hour at room temperature. The organic layer was separated. The organic layer was washed with brine, dried over anhydrous magnesium sulfate, and the desiccant was filtered out. The filtrate was concentrated under reduced pressure. The obtained residue was purified by silica gel column chromatography (ethyl acetate/n-heptane, 5-20%) to obtain the title compound (12.8 g).
ESI-MS m/z 291 [M+H]$^+$ (2) Synthesis of ethyl 5-(4-bromo-2-fluorophenyl)-1-(1,4-dioxaspiro[4.5]decan-8-yl)-1H-pyrazole-4-carboxylate A solution of ethyl 3-(4-bromo-2-fluorophenyl)-3-oxopropanoate (1.5 g) in DMF-DMA (6.89 mL) was stirred at 50° C. for 2.5 hours. The reaction mixture was concentrated under reduced pressure. The residue was dissolved in toluene (7 mL), the obtained solution was concentrated under reduced pressure, and this procedure was repeated. A solution of the residue in ethanol (10 mL) was added to a solution of the (1,4-dioxaspiro[4.5]decan-8-yl)hydrazine hydrochloride obtained in Production Example 5 (3.06 g) and TEA (3 mL) in ethanol (30 mL). After stirring the reaction mixture at 80° C. for 2.5 hours, it was cooled to room temperature. The reaction mixture was concentrated under reduced pressure. Ethyl acetate and water were added to the residue, and the organic layer was distributed. The organic layer was washed with a saturated aqueous sodium hydrogen carbonate solution and brine in that order, dried over anhydrous magnesium sulfate, and the desiccant was filtered out. The filtrate was concentrated under reduced pressure. The residue was purified by silica gel column chromatography (ethyl acetate/n-heptane, 15%) to obtain the title compound (2.10 g).
$^1$H-NMR (400 MHz, CDCl$_3$) δ (ppm): 1.18 (t, J=6.8 Hz, 3H), 1.49-1.60 (m, 2H), 1.73-1.94 (m, 4H), 2.30-2.45 (m, 2H), 3.79-3.89 (m, 1H), 3.90-4.00 (m, 4H), 4.15 (q, J=6.8 Hz, 2H), 7.19 (t, J=8.0 Hz, 1H), 7.40-7.46 (m, 2H), 8.03 (s, 1H).
ESI-MS m/z 475 [M+Na]$^+$ (3) Synthesis of 5-(4-bromo-2-fluorophenyl)-1-(1,4-dioxaspiro[4.5]decan-8-yl)-1H-pyrazole-4-carboxylic acid An 5N aqueous sodium hydroxide solution (2.78 mL) was added to a suspension of ethyl 5-(4-bromo-2-fluorophenyl)-1-(1,4-dioxaspiro[4.5]decan-8-yl)-1H-pyrazole-4-carboxylate (2.1 g) in ethanol (20 mL) and the mixture was stirred at 50° C. for 6 hours. After cooling the reaction mixture to room temperature, the reaction mixture was concentrated under reduced pressure. Water and MTBE were added to the obtained aqueous residue, and the aqueous layer was separated. The obtained aqueous layer was acidified with 5N hydrochloric acid and extracted with ethyl acetate (twice). The combined ethyl acetate extraction layer was washed with water and brine in that order, dried over anhydrous magnesium sulfate, and the desiccant was filtered out. The filtrate was concentrated under reduced pressure to obtain the title compound (2.03 g).

$^1$H-NMR (400 MHz, CDCl$_3$) δ (ppm): 1.48-1.60 (m, 2H), 1.72-1.94 (m, 4H), 2.28-2.45 (m, 2H), 3.77-3.88 (m, 1H), 3.90-3.99 (m, 4H), 7.18 (t, J=8.0 Hz, 1H), 7.39-7.45 (m, 2H), 8.07 (s, 1H).

ESI-MS m/z 449 [M+Na]$^+$ (4) Synthesis of 5-(4-bromo-2-fluorophenyl)-N-(2,4-dimethoxybenzyl)-1-(1,4-dioxaspiro[4,5]decan-8-yl)-1H-pyrazole-4-carboxamide After adding 2,4-dimethoxybenzylamine (747 mg), DIPEA (1.56 mL), HOBT (724 mg) and EDC (1.03 g) to a solution of 5-(4-bromo-2-fluorophenyl)-1-(1,4-dioxaspiro[4.5]decan-8-yl)-1H-pyrazole-4-carboxylic acid (1.90 g) in DMF (40 mL) in that order, the reaction mixture was stirred overnight. The reaction mixture was concentrated to about ⅓ the amount under reduced pressure. Ethyl acetate, water and a saturated aqueous sodium hydrogen carbonate solution were added to the obtained residue, and the organic layer was separated. The organic layer was washed with water and brine in that order, dried over anhydrous magnesium sulfate, and the desiccant was filtered out. The filtrate was concentrated under reduced pressure to obtain the title compound (2.51 g).

$^1$H-NMR (400 MHz, CDCl$_3$) δ (ppm): 1.45-1.60 (m, 2H), 1.65-1.94 (m, 4H), 2.23-2.45 (m, 2H), 3.70-3.80 (m, 1H), 3.75 (s, 3H), 3.80 (s, 3H), 3.90-3.99 (m, 4H), 4.36 (t, J=6.4 Hz, 2H), 5.86 (t, J=6.4 Hz, 1H), 6.38-6.44 (m, 2H), 7.10 (d, J=8.4 Hz, 1H), 7.18 (t, J=8.0 Hz, 1H), 7.34-7.41 (m, 2H), 7.87 (s, 1H).

ESI-MS m/z 574 [M+H]$^+$ (5) Synthesis of 7-bromo-5-(2,4-dimethoxybenzyl)-1-(1,4-dioxaspiro[4,5]decan-8-yl)-1H-pyrazolo[4,3-c]quinoline-4(5H)-one After adding KTB (735 mg) to a solution of 5-(4-bromo-2-fluorophenyl)-N-(2,4-dimethoxybenzyl)-1-(1,4-dioxaspiro[4,5]decan-8-yl)-1H-pyrazole-4-carboxamide (2.51 g) in THF (30 mL) under ice-cooling, the mixture was stirred at the same temperature for 5 minutes and then at room temperature for 2 hours. KTB (400 mg) was further added to the reaction mixture and the mixture was stirred for 40 minutes. A saturated aqueous ammonium chloride solution, ethyl acetate and water were added to the reaction mixture in that order, and the organic layer was separated. The aqueous layer was extracted again with ethyl acetate. The combined organic layer was washed with brine, dried over anhydrous magnesium sulfate, and the desiccant was filtered out and the filtrate was concentrated under reduced pressure. Ethyl acetate (3 mL) and MTBE (9 mL) were added to the obtained residue. The obtained solid was filtered and dried under reduced pressure to obtain the title compound (2.04 g).

$^1$H-NMR (400 MHz, CDCl$_3$) δ (ppm): 1.81 (td, J=14.0, 4.0 Hz, 2H), 1.97-2.06 (m, 2H), 2.15-2.24 (m, 2H), 2.43-2.55 (m, 2H), 3.76 (s, 3H), 4.01 (s, 7H), 4.73-4.83 (m, 1H), 5.50 (brs, 1H), 6.34 (dd, J=8.4, 2.4 Hz, 1H), 6.52 (d, J=2.4 Hz, 1H), 6.99 (d, J=8.4 Hz, 1H), 7.39 (dd, J=8.8, 1.6 Hz, 1H), 7.80 (d, J=1.6 Hz, 1H), 7.82 (d, J=8.8 Hz, 1H), 8.29 (s, 1H).

ESI-MS m/z 576 [M+Na]+

(6) Synthesis of 5-(2,4-dimethoxybenzyl)-7-(2-methoxy-3,5-dimethylpyridin-4-yl)-1-(1,4-dioxaspiro[4.5]decan-8-yl)-1H-pyrazolo[4,3-c]quinoline-4(5H)-one Water (2.5 mL), Pd(PPh$_3$)$_4$ (313 mg) and cesium carbonate (2.64 g) were added to a solution of the (2-methoxy-3,5-dimethylpyridine)boronic acid obtained in Production Example 1 (783 mg) and 7-bromo-5-(2,4-dimethoxybenzyl)-1-(1,4-dioxaspiro[4,5]decan-8-yl)-1H-pyrazolo[4,3-c]quinoline-4(5H)-one (1.50 g) in 1,4-dioxane (10 mL). The reaction mixture was stirred at 130° C. for 3 hours using a microwave reactor. The reaction mixture was cooled to room temperature, and then ethyl acetate and water were added to the reaction mixture and the organic layer was separated. The organic layer was washed with brine, dried over anhydrous magnesium sulfate, and the desiccant was filtered out. The filtrate was concentrated under reduced pressure. The residue was purified by silica gel column chromatography (ethyl acetate/n-heptane, 40%). Ethyl acetate and MTBE were added to the concentrated residue. The obtained solid was filtered and dried under reduced pressure to obtain the title compound (1.52 g).

$^1$H-NMR (400 MHz, CDCl$_3$) δ (ppm): 1.73 (s, 3H), 1.76 (s, 3H), 1.87 (td, J=14.0, 4.0 Hz, 2H), 2.00-2.08 (m, 2H), 2.22-2.32 (m, 2H), 2.49-2.62 (m, 2H), 3.68 (s, 3H), 3.73 (s, 3H), 3.97 (s, 3H), 4.02 (s, 4H), 4.85-4.95 (m, 1H), 5.40-5.60 (m, 2H), 6.29 (dd, J=8.4, 2.4 Hz, 1H), 6.42 (d, J=2.4 Hz, 1H), 6.83 (d, J=8.4 Hz, 1H), 7.05 (d, J=8.4 Hz, 1H), 7.24 (s, 1H), 7.87 (s, 1H), 8.07 (d, J=8.4 Hz, 1H), 8.33 (s, 1H).

ESI-MS m/z 611 [M+H]$^+$ (7) Synthesis of 5-(2,4-dimethoxybenzyl)-7-(2-methoxy-3,5-dimethylpyridin-4-yl)-1-(4-oxocyclohexyl)-1H-pyrazolo[4,3-c]quinoline-4(5H)-one After adding 2N hydrochloric acid (20 mL) to a solution of 5-(2,4-dimethoxybenzyl)-7-(2-methoxy-3,5-dimethylpyridin-4-yl)-1-(1,4-dioxaspiro[4,5]decan-8-yl)-1H-pyrazolo[4,3-c]quinoline-4(5H)-one (1.30 g) in THF (20 mL), the reaction mixture was stirred at room temperature for 19.5 hours. After pouring the reaction mixture into a saturated aqueous sodium hydrogen carbonate solution (60 mL), it was extracted with ethyl acetate. The obtained organic layer was washed with brine, dried over anhydrous magnesium sulfate, and the desiccant was filtered out. The filtrate was concentrated under reduced pressure to obtain the title compound (1.12 g).

$^1$H-NMR (400 MHz, CDCl$_3$) δ (ppm): 1.73 (s, 3H), 1.76 (s, 3H), 2.52-2.87 (m, 8H), 3.68 (s, 3H), 3.74 (s, 3H), 3.97 (s, 3H), 5.27-5.37 (m, 1H), 5.37-5.62 (m, 2H), 6.29 (dd, J=8.8, 2.4 Hz, 1H), 6.42 (d, J=2.4 Hz, 1H), 6.84 (d, J=8.8 Hz, 1H), 7.06 (d, J=8.4 Hz, 1H), 7.28 (s, 1H), 7.88 (s, 1H), 8.10 (d, J=8.4 Hz, 1H), 8.35 (s, 1H).

ESI-MS m/z 567 [M+H]$^+$ (8) Synthesis of 5-(2,4-dimethoxybenzyl)-1-(4-hydroxycyclohexyl)-7-(2-methoxy-3,5-dimethylpyridin-4-yl)-1H-pyrazolo[4,3-c]quinoline-4(5H)-one Sodium borohydride (57.1 mg) was added to a solution of 5-(2,4-dimethoxybenzyl)-7-(2-methoxy-3, 5-dimethylpyridin-4-yl)-1-(4-oxocyclohexyl)-1H-pyrazolo[4,3-c]quinoline-4(5H)-one (570 mg) in THF (20 mL)-methanol (10 mL) under ice-cooling, and the mixture was stirred at the same temperature for 5 minutes and then at room temperature for 1 hour. The reaction mixture was cooled on ice, and 1N hydrochloric acid (2 mL) was added to the reaction mixture. After concentrating the reaction mixture to about ¼ the amount, ethyl acetate and water were added to the residue and the organic layer was separated. The organic layer was washed with a saturated aqueous sodium hydrogen carbonate solution and brine in that order, dried over anhydrous magnesium sulfate, and the desiccant was filtered out. The filtrate was subjected to short silica gel column chromatography (ethyl acetate) to obtain the title compound (597 mg).
ESI-MS m/z 569 [M+H]$^+$ (9) Synthesis of 5-(2,4-dimethoxybenzyl)-7-(2-methoxy-3,5-dimethylpyridin-4-yl)-1-(4-methoxycyclohexyl)-1H-pyrazolo[4,3-c]quinoline-4(5H)-one After adding 60% sodium hydride (dispersion in oil, 31.7 mg) to a solution of 5-(2,4-dimethoxybenzyl)-1-(4-hydroxycyclohexyl)-7-(2-methoxy-3,5-dimethylpyridin-4-yl)-1H-pyrazolo[4,3-c]quinoline-4(5H)-one (300 mg) in THF (5 mL) at 0° C., the mixture was stirred at room temperature for 10 minutes. Iodomethane (0.1 mL) was added to the reaction mixture, and the mixture was stirred at room temperature for 1.5 hours and at 50° C. for 2 hours. Next, iodomethane (0.1 mL) was added to the reaction mixture and it was stirred overnight at 50° C. Water and ethyl acetate were added to the reaction mixture, and the organic layer was separated. The aqueous layer was extracted again with ethyl acetate. The combined organic layer was washed with brine and dried over anhydrous magnesium sulfate, the desiccant was filtered out. The filtrate was concentrated under reduced pressure. The obtained residue was purified by silica gel column chromatography (methanol/chloroform, 2%) to obtain the title compound (110 mg).
ESI-MS m/z 583 [M+H]$^+$

(10) Synthesis of 7-(2-methoxy-3,5-dimethylpyridin-4-yl)-1-(cis-4-methoxycyclohexyl)-1H-pyrazolo[4,3-c]quinoline-4(5H)-one and 7-(2-methoxy-3,5-dimethylpyridin-4-yl)-1-(trans-4-methoxycyclohexyl)-1H-pyrazolo[4,3-c]quinoline-4(5H)-one Triethylsilane (0.09 mL) was added to a solution of 5-(2,4-dimethoxybenzyl)-7-(2-methoxy-3,5-dimethylpyridin-4-yl)-1-(4-methoxycyclohexyl)-1H-pyrazolo[4,3-c]quinoline-4(5H)-one (109 mg) in TFA (1.5 mL), and the reaction mixture was stirred at 60° C. for 4.25 hours. The reaction mixture was concentrated under reduced pressure. Chloroform and a saturated aqueous sodium hydrogen carbonate solution were added to the residue, and the organic layer was separated. The aqueous layer was extracted again with chloroform. The combined organic layer was dried over anhydrous magnesium sulfate, and the desiccant was filtered out. The filtrate was concentrated under reduced pressure. The obtained residue was purified by silica gel column chromatography (chloroform followed by ethyl acetate) to obtain the title compound as a mixture of cis-isomers and trans-isomers (68 mg).

The mixture was dissolved in chloroform (1.1 mL)-ethanol (4.4 mL) and filtered with a Millipore filter. The filtrate was purified by a CHIRALCEL® IB (20 mm Φ×250 mm) by Daicel under conditions of 100% ethanol, 10 mL/min, to obtain the title compound (10.1 mg) of cis-isomer and the title compound of trans-isomer (47.0 mg).
Cis-Isomer
$^1$H-NMR (400 MHz, CDCl$_3$) δ (ppm): 1.63-1.74 (m, 2H), 1.94 (s, 3H), 1.97 (s, 3H), 2.00-2.09 (m, 2H), 2.22-2.30 (m, 2H), 2.47-2.60 (m, 2H), 3.39 (s, 3H), 3.60 (brs, 1H), 4.00 (s, 3H), 4.80-4.89 (m, 1H), 7.06 (dd, J=8.4, 1.6 Hz, 1H), 7.20 (d, J=1.6 Hz, 1H), 7.94 (s, 1H), 8.06 (d, J=8.4 Hz, 1H), 8.30 (s, 1H), 10.42 (brs, 1H).
ESI-MS m/z 433 [M+H]$^+$
Trans-isomer
$^1$H-NMR (400 MHz, CDCl$_3$) δ (ppm): 1.48-1.60 (m, 2H), 1.94 (s, 3H), 1.97 (s, 3H), 2.17-2.40 (m, 6H), 3.32-3.42 (m, 1H), 3.43 (s, 3H), 4.01 (s, 3H), 4.79-4.89 (m, 1H), 7.08 (d, J=8.4 Hz, 1H), 7.25 (s, 1H), 7.94 (s, 1H), 8.04 (d, J=8.4 Hz, 1H), 8.29 (s, 1H), 10.95 (brs, 1H).
ESI-MS m/z 433 [M+H]$^+$ Pharmacological Test Examples A PDE9 Inhibitory Activity Test Example 1) Preparation of a Human Recombinant PDE9 Protein An hsPDE9A 1cDNA fragment was amplified by being based on a base sequence (Accession No.: AF048837) of the hsPDE9A1 registered on GenBank data base, and by using the following sequences (Hokkaido System Science Co., Ltd.) as a primer and Human hippocampus cDNA library (Clontech Laboratories, Inc.) as a template DNA, and using Pfu50 DNA polymerase (Invitrogen Corp.), and by a polymerase chain reaction (PCR) of the following condition.

```
An hPDE9-1 primer:
                                    (SEQ No. 1)
AGGATGGGATCCGGCTCCTCCA An hPDE9A-3 primer:
                                    (SEQ No. 2)
CAGGCACAGTCTCCTTCACTG
```

The condition of PCR: [96° C., 5 min]×1 cycle, [(96° C., 10 sec), (57° C., 5 sec), (72° C., 2 min)]×30 cycles
The obtained hsPDE9A 1cDNA fragment was incorporated in a TOPO-TA cloning vector (Invitrogen Corp.), and the base sequence was checked; and thereafter, the resultant was transfected in a pcDNA 3.1/myc His-tag vector (Invitrogen Corp.) to thereby make a human PDE9 expression vector for mammal cells. The human PDE9 expression vector for mammal cells was transfected with transient expression to an HEK293 cell by using a LIPOFETAMINE 2000 Reagent (Gibco). It was confirmed by Western blot method that the PDE9A expressed in the HEK293 cell, and then, the human PDE9A 1cDNA fragment was transfected in a pYNG vector (Katakura Industries Co., Ltd.) to thereby make an expression vector for insect cells. A supernatant of homogenized silk worm in which a large amount of PDE9 was expressed was purified by an equilibrated Ni column using a buffer A (20 mmol/L Tris-HCl, pH: 8.0, 1 mmol/L DTT, 10 mmol/L imidazole). After 1 hour of mixing of the supernatant and the Ni column, cleaning was carried out using a buffer B (20 mmol/L Tris-HCl, pH: 8.0, 1 mmol/L DTT), and elution was carried out using a buffer C (20 mmol/L Tris-HCl, pH: 8.0, 1 mmol/L DTT, 100 mmol/L imidazole). An elution fraction was preparatively collected to thereby obtain a PDE9 enzyme solution.

2) Measurement of PDE9 Inhibitory Action

To 100 μL of a buffer D (40 mmol/L Tris-HCl, pH: 7.4, 10 mmol/L $MgCl_2$, 1 mM DTT, 2 μM cGMP) solution containing [$^3$H]-cGMP (0.5 μCi/mL), 10 μL of a compound solution for evaluation (a solution in which a compound was dissolved in DMSO and diluted so that the DMSO concentration became 5%) and 90 μL of a solution prepared by diluting the PDE9 enzyme solution prepared in the above with a buffer E (40 mmol/L Tris-HCl, pH: 7.4, 10 mmol/L $MgCl_2$, 1 mM DTT, 1 mmol/L EGTA) were added under ice cooling. The resultant mixed solution was incubated at 30° C. for 10 min, and thereafter heated for 2 min in boiled water to stop the enzyme reaction of the PDE9. Then, the resultant was returned to room temperature; 50 μL of 5'-Nucleotidase (Biomol GmbH, 10 units/mL) was added thereto; and the resultant was incubated at 30° C. for 10 min to thereby convert [$^3$H]-5'-GMP formed in the previous reaction to [$^3$H]-guanosine. 500 μL of an anion exchange resin (Bio-Rad AG1-X2 resin, mesh size: 200-400, $H_2O$:resin=2:1) was added to the resultant reaction liquid, and allowed to stand for 10 min, and thereafter centrifuged (2,000 rpm, 10 min); and a supernatant in which the [$^3$H]-guanosine was present was transferred to a LumaPlate (PerkinElmer, Inc.), and the radioactivity was measured by a TopCount NXT microplate scintillation and luminescence counter (PerkinElmer, Inc.).

The inhibition percentage of the evaluation compound was calculated using the following expression, taking the radioactivity of a control containing no evaluation compound to be (A), the radioactivity of a blank containing no enzyme to be (B), and the radioactivity of the evaluation compound to be (C).

Inhibition percentage=100−{[(C)−(B)]/[(A)−(B)]}×100(%)

The $IC_{50}$ value for PDE9 of the evaluation compound was determined from inhibition percentage for various concentrations. The $IC_{50}$ value in each evaluation compound is shown in the following table 1.

| Example No. | PDE9 IC50 μM |
|---|---|
| 1a | 0.0480 |
| 1b | 0.0136 |
| 1c | 0.0872 |
| 1d | 0.0069 |
| 2a | 0.0116 |
| 2b | 0.0037 |
| 2c | 0.0123 |
| 2d | 0.0013 |
| 3a | 0.0069 |
| 3b | 0.0256 |
| 4a | 0.0058 |
| 4b | 0.0391 |
| 5a | 0.0098 |
| 5b | 0.0127 |

3) Effect on Rodent Cerebrospinal Fluid cGMP

The test compound was administered to ICR male mice (Charles River Laboratories Japan, Inc.), Sprague-Dawley male rats (SD) (Charles River Laboratories Japan, Inc.) or Long-Evans male rats (LE) (Institute for Animal Reproduction), and the cerebrospinal fluid was then collected under pentobarbital anesthesia and stored at −20° C. cGMP in the cerebrospinal fluid was measured in accordance with the acetylation EIA procedure of cGMP EIA kit (GE Healthcare) or the non-acetylation procedure of cGMP EIA kit (Cayman). The result was an increase (C) in the amount of cGMP of the test compound-administered group (B) relative to the amount of cGMP of the vehicle-administered group (A), and was calculated using the following formula.

cGMP increase(C)=[(B)−(A)]/(A)×100(%)

The results are shown in the following table 2.

TABLE 2

| Example No. | % CSF cGMP increase from vehicle control | species | Dose (mg/kg p.o.) | Sampling time (hr) |
|---|---|---|---|---|
| 1b | 147 | rat (LE) | 10 | 2 |
| 1d | 206 | rat (LE) | 10 | 2 |
| 2d | 183 | rat (LE) | 10 | 2 |
| 3a | 200 | rat (LE) | 10 | 2 |
| 5b | 167 | rat (LE) | 10 | 2 |

4) Effect on Rodent Hippocampal cGMP

The test compound was administered to Sprague-Dawley male rats (Charles River Laboratories Japan, Inc.) or Long-Evans male rats (Institute for Animal Reproduction) and then the animals were sacrificed with microwave under pentobarbital anesthesia, and the hippocampus was extracted. After measuring the wet weight, the hippocampus was frozen with liquid nitrogen and stored at −80° C. In the measurement of cGMP in the hippocampus, a 0.5 M perchloric acid/1 mM EDTA solution was added at 5% (w/v) based on the wet weight, and the mixture was homogenized. After the homogenization, the homogenate was centrifuged (10000 rpm, 15 min), and the supernatant was collected. The collected supernatant was neutralized with a 2 M potassium bicarbonate solution and centrifuged (13000 rpm, 10 min). The cGMP concentration in the supernatant was measured in accordance with the non-acetylation EIA procedure of cGMP EIA kit (GE Healthcare). The result was an increase (C) in the amount of cGMP of the test compound-administered group (B) relative to the amount of cGMP of the vehicle-administered group (A), and was calculated using the following formula.

cGMP increase(C)=[(B)−(A)]/(A)×100(%)

The results are shown in the following table 3.

TABLE 3

| Example No. | % hippocampal cGMP increase from vehicle control | species | Dose (mg/kg p.o.) | Sampling time (hr) |
|---|---|---|---|---|
| 1b | 44 | rat (LE) | 10 | 2 |
| 1d | 61 | rat (LE) | 10 | 2 |
| 2d | 23 | rat (LE) | 10 | 2 |
| 3a | 58 | rat (LE) | 10 | 2 |
| 5b | 41 | rat (LE) | 10 | 2 |

The invention claimed is:

1. A compound represented by formula (I), or a pharmaceutically acceptable salt thereof:

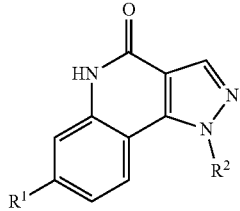

(I)

wherein R$^1$ is a group represented by the formula:

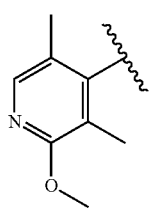 [SMILES: *c1c(C)cnc(OC)c1C]

a group represented by the formula:

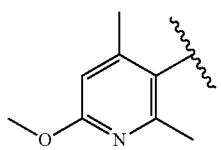 [SMILES: *c1c(C)cc(OC)nc1C]

or a group represented by the formula:

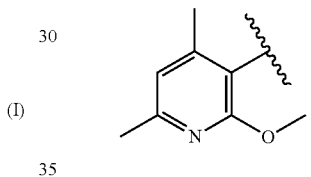

and R$^2$ is a 3-methyltetrahydro-2H-pyran-4-yl group or 4-methoxycyclohexyl group.

2. The compound or pharmaceutically acceptable salt thereof according to claim 1, wherein the compound is represented by formula (II):

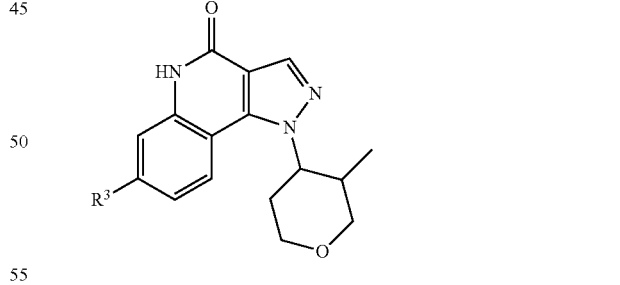

(II)

wherein R$^3$ is a group represented by the formula:

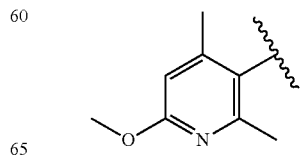

or a group represented by the formula:

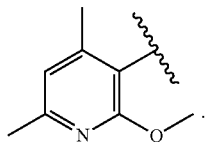

3. The compound or pharmaceutically acceptable salt thereof according to claim 1, wherein the compound is represented by formula (III):

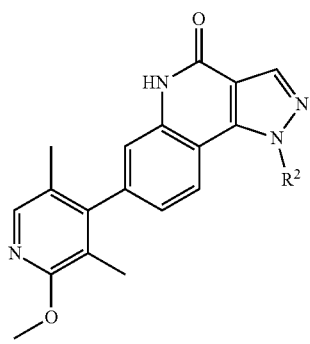

(III)

wherein R² is a 3-methyltetrahydro-2H-pyran-4-yl group or 4-methoxycyclohexyl group.

4. The compound or pharmaceutically acceptable salt thereof according to claim 1, wherein the compound is (-)-7-(6-Methoxy-2,4-dimethylpyridin-3-yl)-1-((3R*,4R*)-3-methyltetrahydro-2H-pyran-4-yl)-1H-pyrazolo[4,3-c]quinoline-4(5H)-one ((-)-cis):

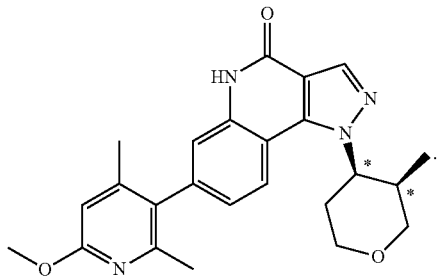

* relative stereochemistry chiral

5. The compound or pharmaceutically acceptable salt thereof according to claim 1, wherein the compound is (-)-7-(6-Methoxy-2,4-dimethylpyridin-3-yl)-1-((3R*,4S*)-3-methyltetrahydro-2H-pyran-4-yl)-1H-pyrazolo[4,3-c]quinoline-4(5H)-one ((-)-trans):

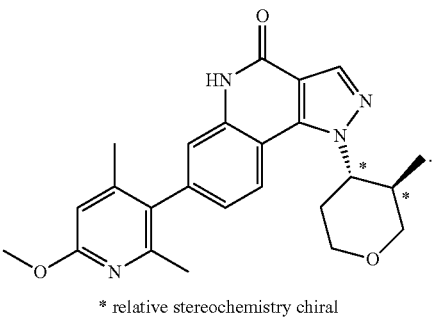

* relative stereochemistry chiral

6. The compound or pharmaceutically acceptable salt thereof according to claim 1, wherein the compound is (-)-7-(2-Methoxy-4,6-dimethylpyridin-3-yl)-1-((3R*,4S*)-3-methyltetrahydro-2H-pyran-4-yl)-1H-pyrazolo[4,3-c]quinoline-4(5H)-one ((-)-trans):

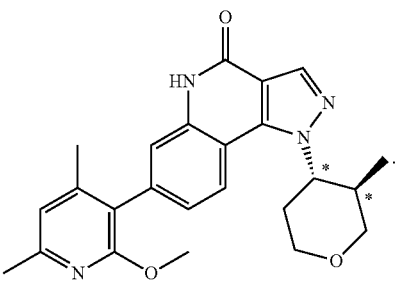

* relative stereochemistry chiral

7. The compound or pharmaceutically acceptable salt thereof according to claim 1, wherein the compound is (-)-7-(2-Methoxy-3,5-dimethylpyridin-4-yl)-1-((3R*,4R*)-3-methyltetrahydro-2H-pyran-4-yl)-1H-pyrazolo[4,3-c]quinoline-4(5H)-one ((-)-cis):

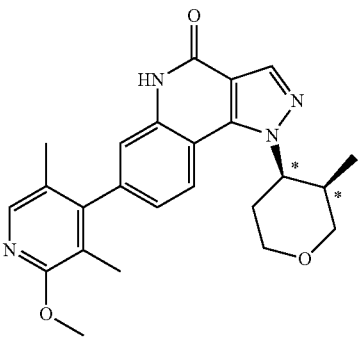

* relative stereochemistry chiral

8. The compound or pharmaceutically acceptable salt thereof according to claim 1, wherein the compound is 7-(2-Methoxy-3,5-dimethylpyridin-4-yl)-1-(trans-4-methoxycyclohexyl)-1H-pyrazolo[4,3-c]quinoline-4(5H)-one:

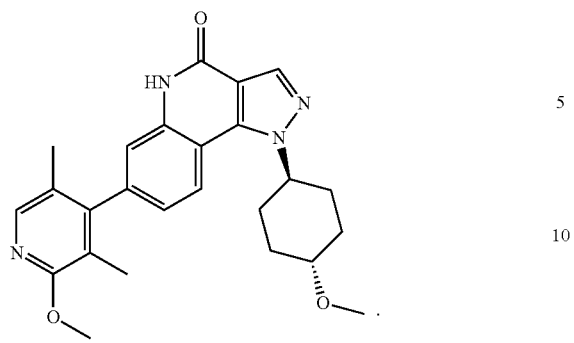

9. A pharmaceutical composition comprising the compound or pharmaceutically acceptable salt thereof according to claim 1 as an active ingredient.

10. A method for improving cognitive impairment in Alzheimer's disease in a patient in need thereof, comprising administering the compound or pharmaceutically acceptable salt thereof according to claim 1 to the patient.

11. A method for increasing intracerebral cGMP concentration in a patient in need thereof, comprising administering the compound or pharmaceutically acceptable salt thereof according to claim 1 to the patient.

* * * * *